(12) United States Patent
Kato et al.

(10) Patent No.: US 6,236,042 B1
(45) Date of Patent: *May 22, 2001

(54) METHOD AND APPARATUS FOR DIRECT COUPLING OF LIQUID CHROMATOGRAPH AND MASS SPECTROMETER, LIQUID CHROMATOGRAPHY-MASS SPECTROMETRY, AND LIQUID CHROMATOGRAPH-MASS SPECTROMETER

(75) Inventors: Yoshiaki Kato, Mito; Tadao Mimura, Katsuta, both of (JP)

(73) Assignee: Hitachi, Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/499,318

(22) Filed: Feb. 7, 2000

Related U.S. Application Data

(63) Continuation of application No. 08/707,578, filed on Sep. 5, 1996, now Pat. No. 5,859,432, which is a continuation of application No. 08/355,223, filed on Dec. 9, 1994, now Pat. No. 5,581,081.

(30) Foreign Application Priority Data

Dec. 9, 1993 (JP) .................................................... 5-308875

(51) Int. Cl.$^7$ ............................. G01D 59/44; H01J 49/00
(52) U.S. Cl. ............................................ 250/288; 250/281
(58) Field of Search .................................. 250/281, 282, 250/288

(56) References Cited

U.S. PATENT DOCUMENTS

| | | | |
|---|---|---|---|
| 4,991,291 | * 2/1991 | Tou | 250/288 |
| 5,170,052 | * 12/1992 | Kato | 250/288 |
| 5,235,186 | * 8/1993 | Robins | 250/288 |
| 5,266,192 | * 11/1993 | Ligon et al. | 250/288 |
| 5,304,798 | * 4/1994 | Tomany et al. | 250/288 |
| 5,352,892 | * 10/1994 | Mordehai et al. | 250/288 |
| 5,412,208 | * 5/1995 | Covey et al. | 250/288 |
| 5,504,327 | * 4/1996 | Sproch et al. | 250/288 |

\* cited by examiner

Primary Examiner—Bruce C. Anderson
(74) Attorney, Agent, or Firm—Kenyon & Kenyon

(57) ABSTRACT

A nebulized jet from a nebulizer is subjected to mechanical agitation and stirring to render the mists uniform and fine, then the droplets of the mists thus rendered uniform and fine are ionized. By accelerative collision of the resulting ions in a medium pressure chamber it is made possible to effect desolvation efficiently. Consequently, chemical noises caused by cluster ions can be greatly diminished and it is possible to attain high sensitive measurement of a sample in atmospheric pressure ionizations LC/MS.

4 Claims, 14 Drawing Sheets

A-A' SECTION

METHOD AND APPARATUS FOR DIRECT COUPLING OF LIQUID CHROMATOGRAPH AND MASS SPECTROMETER, LIQUID CHROMATOGRAPHY-MASS SPECTROMETRY, AND LIQUID CHROMATOGRAPH-MASS SPECTROMETER

This is a continuation of application Ser. No. 08/707,578, filed Sep. 5, 1996 now U.S. Pat. No. 5,859,432, which is a division of application Ser. No. 08/355,223, filed Dec. 9, 1994 now U.S. Pat. No. 5,581,081, the entirety of which is incorporated herein by reference.

BACKGROUND OF THE INVENTION

1. Field of the Invention

The present invention relates to a method and apparatus for direct coupling of a liquid chromatograph and a mass spectrometer, liquid chromatography—mass spectrometry, and a liquid chromatograph; mass spectrograph.

2. Description of the Prior Art

A mass spectrometer (MS) is a highly sensitive analysis instrument which provides the user with information on the molecular weight and structure of organic compounds and which is therefore indispensable in the fields of organic chemistry, pharmacy and biochemistry. However, MS cannot separate and distinguish the components of a mixture, and therefore when it is a mixture that is to be analyzed, analysis has been difficult. In view of this point, a liquid chromatograph direct coupled mass spectrometer (LC/MS) has been proposed, using a liquid chromatograph (LC) which is superior in separating and distinguishing a mixture, and utilizing the point that non-volatile substances, thermally unstable substances, inorganic and organic compounds, low and high molecular weight substances can be analyzed easily if only they are soluble in solvents.

LC is a device for mixing a sample for analysis with a solvent and separating the mixture under atmospheric pressure, while MS is a device for analyzing an ionized sample in high vacuum. For coupling the two, therefore, it is necessary to remove the solvent (desolvation) from LC effluent, then ionizing the sample remaining after desolvation and feeding the ionized sample to MS held in high vacuum. A technique for coupling LC and MS is described, for example, in Japanese Patent Publication No.43692/83, in which effluent from LC is nebulized, the resulting mists are desolvated and ionized, and the thus-ionized sample (desolvated effluent) is subjected to mass spectrometric analysis.

Once the effluent from LC is nebulized, the nebulized jet spreads like spray. In this case, mists of relatively large droplets gather at the center of the jet and in the vicinity thereof, while mists of relatively small droplets gather at the marginal portion and in the vicinity thereof. With movement of these mists, the mists of large droplets present centrally and thereabouts are not so greatly influenced by air, etc. because their mass and kinetic energy are large, so that they are not vaporized so much nor do they become so small in droplet diameter. On the other hand, the mists of small droplets present along and near the marginal portion are influenced directly by air, etc. because their mass and kinetic energy are small, so that they become smaller in droplet diameter gradually due to fluid resistance and repeated collision with other droplets, etc. As the droplet diameter becomes smaller, the mists are influenced more greatly by air, etc. and the moving speed becomes lower, that is, the duration of influence becomes longer. As a result, the vaporization of the small droplets present along and near the marginal is promoted more and more to render the droplet diameter smaller.

Thus, when the effluent from LC is nebulized and with movement of the resulting mists, the mists of large droplets present centrally and thereabouts do not vary so greatly in droplet diameter, while the mists of small droplets present along and near the marginal portion become smaller in droplet diameter, so that variations in droplet diameter become larger as a whole.

Also known is the technique of making finer a nebulized effluent (a mixed sample-solvent solution) from a chromatograph and then removing the solvent from the mists. For making droplets fine, there often is adopted a heating method which is simple in structure, merely involving heating droplets using a vaporizer. For example, the vaporizer is constituted by a metallic block containing a heater so as to permit substantially uniform heating, such as a quartz tube with heating wire wound thereon. Nebulized jet (effluent from a chromatograph) is heated by radiant heat from the vaporizer while it passes through a vaporizing space surrounded with the vaporizer. A marginal flow of the nebulized jet is lower in moving speed than a central flow due to friction with the wall surface of the vaporizer and can be supplied with a larger amount of heat from the wall surface because of its closer position to the wall surface. More particularly, the marginal droplets absorb infrared rays emitted from the surrounding wall surface, whereby the vaporization of liquid from the droplet surfaces is accelerated to promote the micronization of droplets. Most of the infrared rays is consumed for the micronization of mists in the marginal flow and does not reach the central flow of mists. Therefore, the central droplets cannot be heated to a satisfactory extent. Since the mists in the marginal portion are originally small in droplet diameter due to spray-like diffusion and absorb a larger amount of radiant heat, the diameter of the marginal droplets decreases rapidly. Conversely, droplets larger in diameter are concentrated on the central portion. For this reason, the distribution width, of droplet diameters in the nebulized jet becomes larger during movement through the vaporizing space than at the time when the mists were generated. Thus, according to the heating method, fine mists gather in the marginal portion, while mists larger in diameter are present centrally in a larger proportion, rather presenting larger variations in the distribution of droplet diameters.

The nebulized effluent is further subjected to desolvation. For example, by the application of heat, only sample is extracted from a mixed sample-solvent solution. If the distribution range (scatter or variations) of droplet diameters is wide, there arises a problem. Particularly, giant droplets pose a problem. More particularly, if desolvation is performed under severe conditions (overheating and accelerative collision of ions with high energy) for the desolvation of large-diameter droplets, it is indeed possible to extract sample from the mixed solution containing the large droplets, but the droplets smaller in diameter pass the desolvation and undergo thermal decomposition or are converted into fragment ions, which cannot be analyzed. On the other hand, if desolvation is performed under mild conditions (low heat and accelerative collision of ions with low energy) so as to prevent thermal decomposition, etc. of droplets smaller in diameter, the desolvation of the larger droplets becomes insufficient and if they are introduced into MS, they are detected as noise, thus resulting in deterioration of the analytical sensitivity.

It is an object of the present invention to attain a highly sensitive mass spectrometry while avoiding the damage of sample such as thermal decomposition.

In connection with LC/MS interface, atmospheric pressure ionization (API) has come to be used widely. According to API, effluent from a liquid chromatograph is ionized under atmospheric pressure by such as method as electrospray (ESI) for example. The resulting ions are conducted into a chamber called medium pressure chamber. In the medium pressure chamber, upon change in pressure from atmospheric to vacuum, under evacuation using a vacuum pump, the ions introduced into -the same chamber undergo adiabatic expansion due to sudden drop of pressure and is cooled rapidly, whereby a polar molecule, e.g. water, is added to the ions to form cluster ions. The cluster ions are desolvated for mass spectrometry. For example, an ion drift voltage is applied to the cluster ions to induce acceleration and repeated collision of the ions with neutral molecules, and the energy of this collision is taken into the interior to remove the added polar molecules (desolvation by collision-induced dissociation).

Unless the cluster ions are desolvated to a thorough extent, a chemical noise will be generated. This chemical noise will be explained below.

Sometimes there appear peaks at equal intervals on mass spectrum. These peaks correspond to chemical noises caused by cluster ions. Particularly, noises induced by cluster ions of water appear in a large number with high intensity. Also, noises sometimes appear due to the addition of water molecules to molecular ions of a sample. In this case, one ion species is dispensed into several ion species, so that the ion current value of the molecular ions which are to be detected becomes lower. The development of such cluster ions can be suppressed by heating mists to a thorough extent in ionization to vaporize sample and solvent to a perfect extent or by heating the whole of the interface. However, if all droplets are to be vaporized by heating, small-diameter droplets will continue to undergo heat for a long time after vaporization. Such excess heating will cause thermal decomposition of the sample molecules, resulting in loss of all information on the molecular weight and structure of the sample, and hence the mass spectrometry, or analysis as LC/MS, of the sample which is to be detected can no longer be effected.

On the other hand, the applied heat is consumed for the vaporization of added molecules from cluster ions and droplets to prevent the rise in temperature of molecules or ions and hence prevent thermal decomposition thereof. Mist is a mixture of droplets and gas, so even if mist is heated, the heat is consumed for the vaporization of solvent from the droplet surface, so that the mist temperature does not rise. Consequently, even a thermally unstable substance fed from LC can be sent stably in the state of mist to an atmospheric pressure ion source. Also for this reason, excess heating of mist must be avoided.

For the purpose of diminishing chemical noises induced by cluster ions and prevent thermal decomposition of sample molecules, a precise temperature control for the heating section has been tried. However, it is necessary to perform a best-point searching operation for each object to be measured and thus the trouble of measurement is enhanced markedly.

Further, various sizes of cluster ions and neutral droplets are included, so in the event giant droplets are included, the desolvation in the intermediate pressure chamber by heating and heat-collision of ions becomes insufficient. If the desolvation is performed under severe conditions (overheating and accelerative collision of ions with high energy), small clusters will be decomposed thermally or transformed into fragment ions though the desolvation of large clusters will be sufficient. And if the desolvation is conducted under mild conditions, large clusters and droplets will not be desolvated to a satisfactory extent. Moreover, if large droplets having electric charge or neutral droplets are introduced into MS, vaporization is performed continually while flying through the intermediate pressure chamber and the mass spectrometric portion and they are detected as the foregoing chemical noises by means of a detector. Besides, a large amount of cluster ions appears in a wide mass area and masks the ions of the sample component to be analyzed. As a result, the noise level rises greatly to the extent that highly sensitive analysis is no longer feasible.

It is another object of the present invention to avoid heating sample molecules to a high temperature, and thereby prevent thermal decomposition thereof and provide a mass spectrum of good quality, and furthermore prevent the development of cluster ions and make highly sensitive LC/MS measurement possible.

In connection with LC/MS interface and atmospheric pressure ionization, special attention has been paid to atmospheric pressure chemical ionization (APCI) from the standpoint of wide application range and stability, and APCI has come to be used widely. For example, APCI is described in Analytical Chemistry, Vol.62, No.13 (1990), pp.713A–725A, and Journal of Chromatographic Science, Vol.29 (1891), pp.357–366. In APCI, effluent (a mixed sample-solvent solution) from a liquid chromatograph is nebulized under atmospheric pressure and the resulting mists are exposed to corona discharge at a high voltage of about 3 to 5 kV (using a needle electrode for corona discharge), whereby first solvent molecules are ionized. The ions thus produced repeat ion-molecule reaction with sample molecules, and eventually the sample molecules are ionized. The thus ionized sample is conducted to a mass spectrometer in high vacuum and is subjected to mass spectrometric analysis.

When the effluent from the liquid chromatograph is fed to the vicinity of the needle electrode for corona discharge, if there are large variations in droplet diameter of the mists as mentioned above, there is created a complicated flow. Consequently, the mist flow near the said needle electrode varies continually. As a result, the ion-molecule reaction becomes unstable and it becomes impossible to ensure a stable supply of ionized sample to the mass spectrometer.

Also in APCI, heating the mists of effluent from the liquid chromatograph for micronization is effective in accelerating the subsequent ion-molecule reaction. In this case, however, there will occur not only a great difference in density (variations in droplet diameter) but also a difference in temperature of the nebulized jet, as noted previously. If the nebulized jet having such a temperature difference is fed to the vicinity of the needle electrode for corona discharge, the temperature around the needle electrode will vary continually, also resulting in the ion-molecule reaction becoming unstable. Accordingly, the ionized sample can no longer be fed stably to the mass spectrometer and it becomes impossible to make high sensitive analysis.

It is a further object of the present invention to stabilize the mists of effluent to be fed from a liquid chromatograph to a needle electrode for corona discharge, thereby stabilize the ion-molecule reaction of sample and solvent and make highly sensitive LC/MS measurement possible.

SUMMARY OF THE INVENTION

According to the present invention, in order to achieve the above-mentioned objects, in nebulizing the effluent from the liquid chromatograph, then desolvating and ionizing the mists and subjecting the ionized sample to mass spectrometric analysis, the mists are stirred.

According to the present invention, in order to achieve the abovementioned objects, in nebulizing and ionizing the effluent from the liquid chromatograph under atmospheric pressure, followed by desolation and mass spectrometric analysis in high vacuum, the mists are stirred.

According to the present invention, in order to achieve the foregoing objects, in nebulizing the effluent from the liquid chromatograph, then desolvating and ionizing the mists and subjecting the thus-ionized sample to mass spectrometric analysis, a portion of the mists is selected and subjected to desolvation and ionization.

According to the present invention, in order to achieve the foregoing objects, in nebulizing the effluent from the liquid chromatograph, then heating the mists, desolvating and ionizing the heated mists and subjecting the thus-ionized sample to mass spectrometric analysis, there is used a means for conducting the heat from the source of that heating to further heat the mists.

According to the present invention, in order to achieve the foregoing objects, in nebulizing the effluent from the liquid chromatograph under atmospheric pressure, then ionizing the mists by corona discharge, followed by desolvation and mass spectrometric analysis in high vacuum, the mists are stirred.

According to the above constructions, for example by changing the direction of mist flow mechanically, the mists are stirred and the vaporization of central large droplets is promoted for micronization. Particularly, if the temperature of the marginal mist flow is high, the vaporization will be accelerated to a greater extent. At this time, moreover, the marginal and central flows change places with each other and infrared rays radiated from the surrounding heated wall surface are absorbed uniformly and efficiently by the whole of the mists to make the mists finer.

Besides, the stirring of the mists can be done more effectively by a turbulent flow created behind an object placed in the nebulized jet. As a result, the micronization of droplets is promoted not only by the agitation of the mists but also by a mechanical force of the turbulent flow.

Moreover, by once dividing the mists and then stirring them again, it is made possible to make the mists uniform in temperature and finer in size.

By ionizing uniform and fine droplets and thereafter introducing the thus-ionized droplets into MS, the desolvation of cluster ions by accelerative collision-induced dissociation in the medium pressure portion can be done efficiently, whereby chemical noises derived from cluster ions can be diminished to a great extent. As a result, stable and highly sensitive LC/MS analysis can be realized.

Further, the marginal flow of the nebulized jet containing a high proportion of fine droplets and having a high temperature is introduced into an atmospheric pressure ion source for example and is ionized therein. The resulting ions (including cluster ions) are introduced into the medium pressure chamber and desolvation is performed efficiently by accelerative collision-induced dissociation using an ion drift voltage.

That the temperature is high even slightly mitigates the cooling by adiabatic expansion and makes desolvation effective. As a result, chemical noises derived from cluster ions can be diminished greatly and it becomes possible to make highly sensitive analysis. Even if the solvent composition changes every moment in gradient analysis or the like, the desolvation in the medium pressure chamber can be done efficiently because only the micronized marginal portion is ionized and taken in.

Further, for example by finely dividing the nebulized jet mechanically and greatly increasing the area of the heated wall surface, infrared rays radiated from the heated wall surface can be absorbed efficiently up to the interior of the nebulized jet. As a results, the mist droplets can be made finer and uniform and it is possible to attain uniforming of temperature.

Consequently, particularly the accelerative collision-induced dissociation in the medium pressure portion is done efficiently and chemical noises derived from cluster ions can be diminished to a great extent. As a result, not only stable and high sensitive analysis can be realized, but also stable measurement is ensured also in gradient analysis involving everchanging solvent composition.

Further, for example by changing the mist flow mechanically, the mists are stirred together to accelerate the vaporization of the central droplets for micronization. Consequently, the mist flow fed to the needle electrode for corona discharge becomes stable to stabilize the chemical ionization of sample and solvent, whereby ionized sample can be fed stably to the mass spectrometer. As a result, sensitivity is improved.

DETAILED DESCRIPTION

Embodiments of the present invention will be described below with reference to the accompanying drawings.

Figure 1:
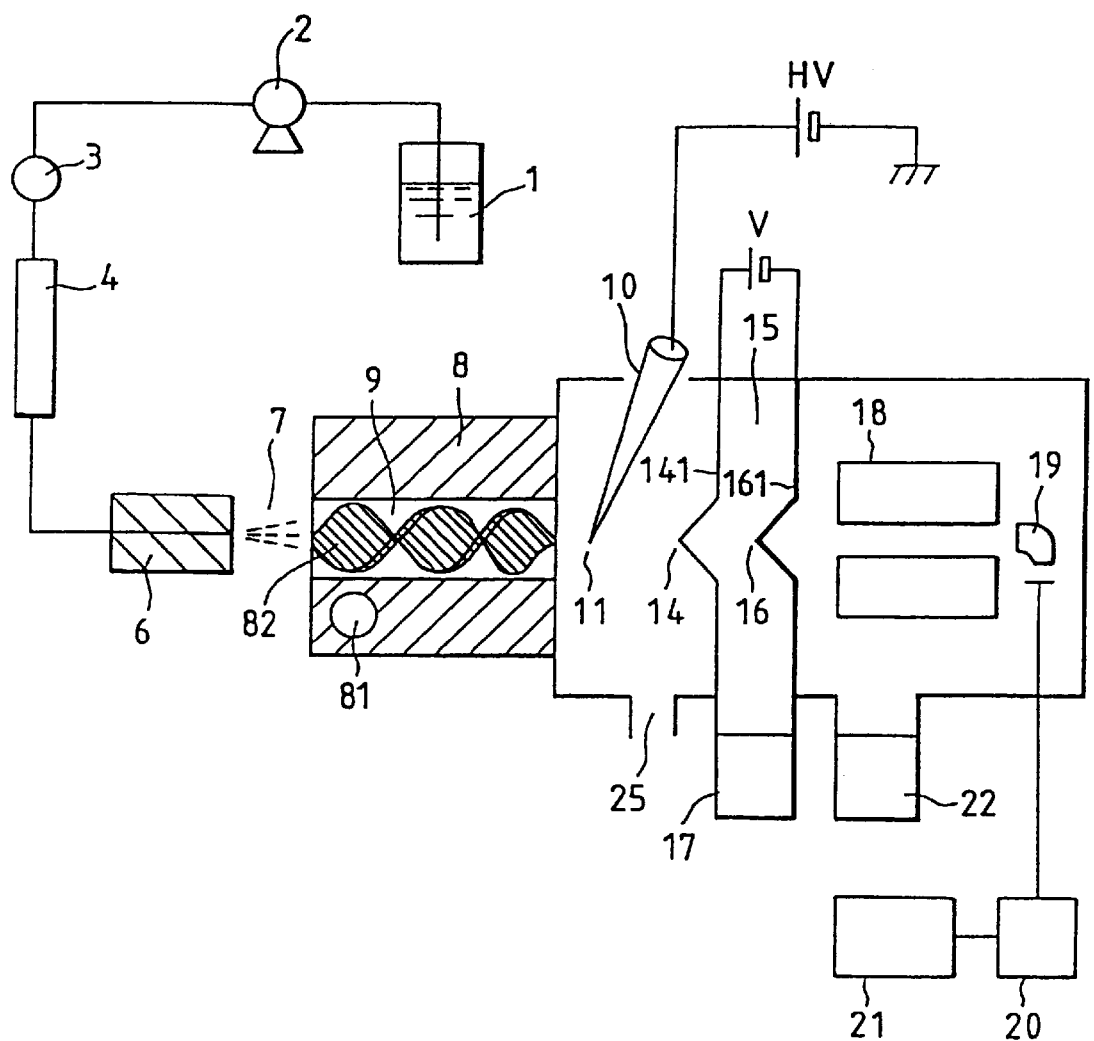
FIG. 1 is a diagram showing the whole of LC/MS according to embodiment 1 of the present invention.
Figure 2A:
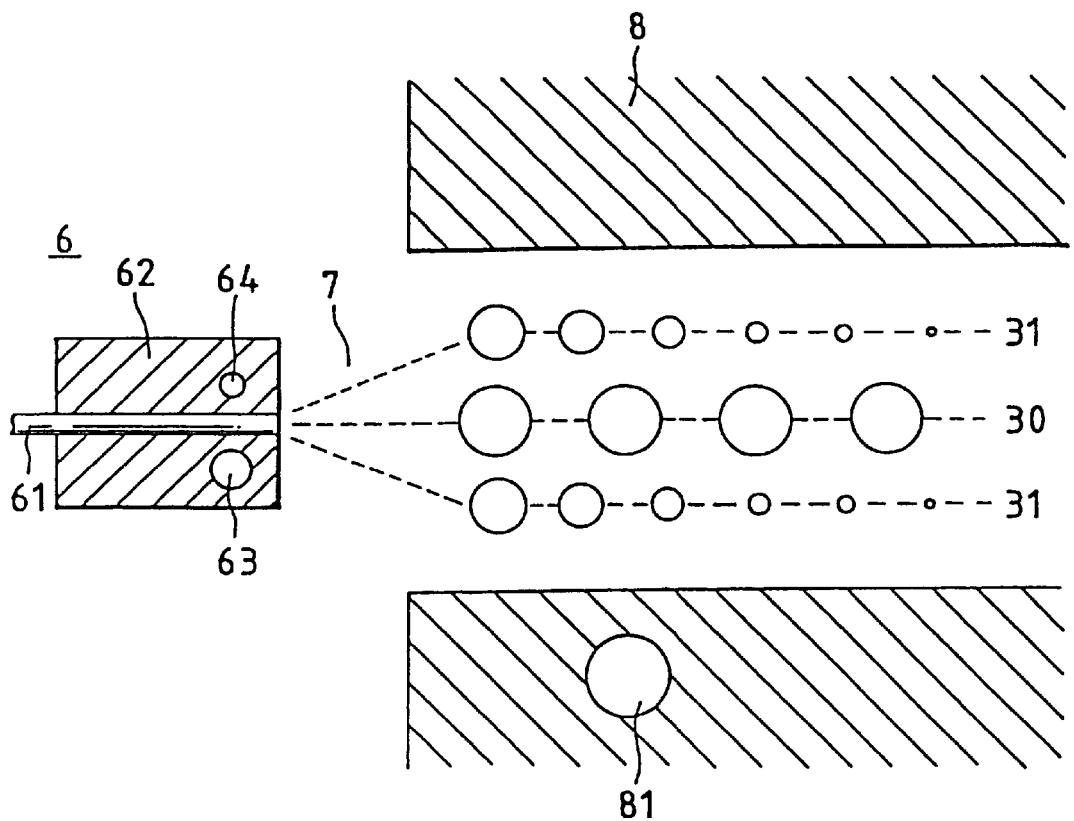
FIGS. 2(a) and (b) are diagrams showing a thermal nebulizer and a vaporizer.
Figure 2B:
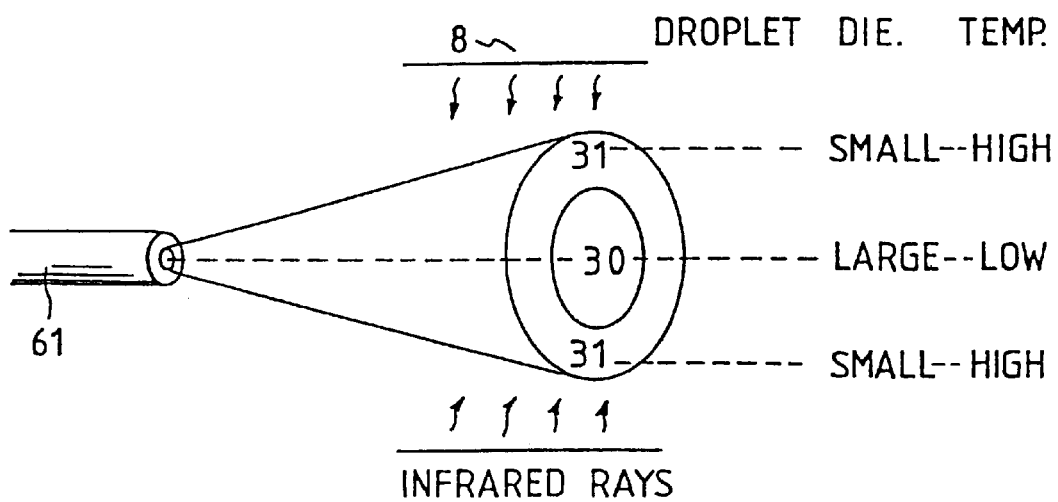

FIG. 1 is an explanatory diagram showing LC/MS (incl. interface) according to the first embodiment of the present invention, and FIG. 2 is an enlarged diagram of a nebulizer and a vaporizer. In both figures, the reference numeral 1 denotes a mobile phase for separating sample components, numeral 2 denotes a pump, numeral 3 denotes a sample inlet for the introduction of a sample solution, numeral 4 denotes an analyzing column, numeral 6 denotes a nebulizer, numeral 7 denotes a nebulizing space of atmospheric pressure, numeral 8 denotes a vaporizer, numeral 81 denotes a heater, numeral 82 a spiral insertion rod, numeral 9 a vaporizing space, numeral 9 a needle electrode for corona discharge with high voltage applied thereto, numeral 11 an atmospheric pressure chemical ion source, numeral 14 a first fine hole for ion sampling, numeral 15 a medium pressure portion, numeral 16 a second fine hole, numeral 17 a vacuum pump for evacuating the intermediate pressure portion, numeral 18 a mass spectrometric analysis portion, numeral 19 a detector, numeral 20 a DC amplifier, numeral 21 a data processing portion, numeral 22 a vacuum pump for evacuating the mass spectrometric analysis portion, numeral 30 a central axis of a nebulized jet, and numeral 31 a marginal flow of the nebulized jet.

In FIG. 1, the mobile phase (solvent) 1 stored in a mobile phase tank is delivered by the pump 2, while a sample solution is introduced through the sample inlet 3 using a microsyringe or the like and is fed to the analyzing column 4 by the mobile phase 1 which is flowing continuously. The sample thus fed is separated component by component in the analyzing column 4 and the eluted components are fed to the nebulizer 6 through a pipe.

Various nebulizers are available. Reference is here made to the one illustrated in FIG. 2(a). The nebulizer 6 comprises a metallic capillary of 0.1 mm or so in inside diameter, a heat block 62 which surrounds the metallic capillary 61, a heater 63 and a temperature sensor 64. The metallic capillary 61 of the nebulizer 6 is heated through the heat block 62 which is heat-controlled by the heater 63 and the temperature sensor 64. Eluate is fed to the metallic capillary 61 and is heated to 200° C. or so at a stretch, then is ejected as mists from the front end of the metallic capillary 61 into the nebulizing space 7 at atmospheric pressure. The nebulized jet passes through the nebulizing space 7 and enters the heated nebulizing space 9 of the vaporizer 8 while being diffused gradually. During this diffusion, fine droplets gather in the marginal portion 31 under heating from the surroundings, while in the central portion 30 are present droplets of larger diameters in a higher proportion. The details of this phenomenon will be described later. Referring again to FIG. 1, the mists which have passed through the vaporizer 8 enter the atmospheric pressure ion source 11, in which solvent molecules are first ionized by corona discharge from the front end of the needle electrode for corona discharge with a high voltage of 3 to 5 kV applied thereto. The resulting ions then repeat the ion-molecule reaction with the sample and eventually ionize the sample molecules. The ions obtained are introduced through the first fine hole 14 into the medium pressure portion 15. At this time, there occurs a pressure change from atmospheric pressure to a medium vacuum, so that the ions are cooled and cluster ions are formed. The cluster ions are accelerated by a drift voltage V applied to first and second partition walls 141, 161 and impinge on neutral molecules. This impingement is repeated many times and a portion of the impingement energy is taken in to heat the ions, whereby the added molecules are split off (desolvation by collision-induced dissociation). Uniform and fine droplets (cluster ions) are desolvated efficiently at this stage. Bare ions after desolvation pass through the second fine hole 16 and enter the mass spectrometric analysis portion 18, in which the ions undergo mass scattering. The ions are then detected by the detector 19, pass through the DC amplifier 20 and enter the data processor 21, which in turn provides a mass spectrum.

The following description is now provided about a basic structure of the LC/MS interface portion in APCI.

The LC/MS interface portion in APCI mainly comprises (1) nebulizing means, (2) mist micronizing means, (3) ionizing means, (4) cluster ion desolvating means and (5) means for introducing ions into MS portion.

(1) Nebulization

A solution (effluent from chromatograph/mixed sample-solvent solution) is nebulized into the nebulizing space 7 at atmospheric pressure with the aid of gas current, heating or ultrasonic vibration. Nebulization is a good means for stably shifting many thermally unstable substances present in liquid to gas phase. Mist is a mixture of gas and liquid. Even if mists are heated, the temperature thereof does not rise because the heat is consumed as the vaporization heat of solvent until complete vaporization of the mists into gas. For this reason there is obtained an advantage that a thermally unstable substance can be shifted stably to gas phase. The eluate from the analyzing column 4 is fed to the metallic capillary 61 and is heated at a stretch to 200° C. or so therein, then is ejected as mists from the front end of the capillary 61 into the nebulizing space 7 at atmospheric pressure. The mists pass through the space 7 and enter the heated vaporizing space 9 of the vaporizer 8 while being diffused gradually. Generally, the mists ejected from the metallic capillary 61 are distributed widely in droplet diameter from 100 to 1 μm. Since the diffusion rate of vaporized molecules and fine droplets is higher than that of relatively large droplets, a high proportion of such fine droplets are present in the marginal portion 31 of the nebulized jet. Conversely, large droplets are present in and near the central portion 30 of the same jet. This state is as shown in FIG. 2(a).

(2) Micronization of Mists

Figure 3:
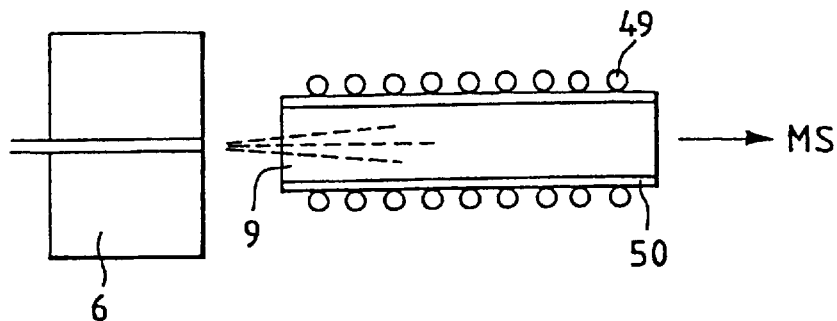
FIG. 3 is a diagram showing the details of the vaporizer.

Giant molecules of 100 μm or so obstruct ionization and cause chemical noises in the subsequent process. Therefore, it is necessary that large droplets be made fine to a sufficient extent prior to ionization. For the micronization of droplets there often is adopted a heating method which is simple in structure. Heating is effective in decreasing the degree of cooling by adiabatic expansion in the medium pressure chamber 15. As shown in FIG. 2, the vaporizer 8 is constituted by a metallic block or the like containing a heater 81 so as to permit substantially uniform heating for the vaporizing space 9 having, say, a diameter of 5 mm and a length of 50 mm. The vaporizer 8 may be of such a structure as shown in FIG. 3 in which a heating wire 49 is wound round a quartz tube 50 having a length of 50 mm and an inside diameter of 5 mm. The vaporizing space 9 is formed rectilinearly so that mists can reach the atmospheric pressure ion source 11 smoothly. The nebulized jet from the metallic capillary 61 is heated by the radiant heat from the vaporizer 8 during passing through the vaporizing space 9. In this case, the marginal flow 31 of the nebulized jet is supplied with a larger amount of heat because its moving speed is lower than that of the central flow 30 due to friction with the wall surface of the vaporizer and also because it is close to the wall surface. That is, the droplets in the marginal portion 31 absorb infrared rays radiated from the wall surface, whereby the vaporization of liquid from the droplet surfaces is greatly promoted and hence the micronization of droplets is promoted. On the other hand, as to the central portion 30, most of the infrared energy is consumed for the micronization of mists in the marginal flow and does not reach the central mist flow, so the droplets in the central portion 30 are not heated to a sufficient extent.

Thus, the droplets in the marginal portion absorb a larger amount of radiant heat, in addition to their originally small diameters due to diffusion after nebulization, and hence they decrease in diameter rapidly. In contrast therewith, droplets larger in diameter are concentrated on the central portion 30. Consequently, the distribution width (scatter) of droplet diameters in the nebulized jet becomes larger as the mists move through the vaporizing space 9 from the time when they were formed. That is, in the marginal portion 31 the temperature is high and fine mists gather, while in the central portion 30 the temperature is low and large-diameter mists are present in a high proportion. This state is as shown in FIGS. 2(a) and (b).

(3) Ionization

The fine mists and solvent molecules after passing through the vaporizer 8 enter the atmospheric pressure ion source 11 in a mixed state, in which the solvent molecules are first ionized by corona discharge from the front end portion of the corona discharge needle electrode 10 with a high voltage of 3 to 5 kV applied thereto. The resulting ions then repeat ion-molecule reaction with sample molecules and eventually ionize the sample molecules.

(4) Desolvation of Cluster Ions

The ions thus formed pass through the first fine hole 14 formed nearly centrally of a partition wall 141 which constitutes one wall surface of the atmospheric pressure ion source 11 and which is positioned on the side opposite to the vaporizer 8; the ions then are introduced into the medium pressure portion 15 which are evacuated by the vacuum pump 17. The ions thus introduced are cooled rapidly by adiabatic expansion caused by sudden drop of pressure to form cluster with polar molecules, e.g. water, added thereto. The cluster ions are accelerated by the ion drift voltage V applied between the partition walls 141 and 161 and repeat collision with neutral molecules. A portion of this collision energy is taken in, so that the cluster ions are heated and the added molecules are removed. This is called desolvation by collision-induced dissociation. Molecules of low molecular weight which have entered the medium pressure chamber 15 are diffused and evacuated by the vacuum pump 17.

(5) Introduction of Ions into MS Portion

The ions thus desolvated then pass through the second fine holes 16 formed nearly centrally of the partition wall 161 and enter the mass spectrometric analysis portion 18, in which they undergo mass scattering. The ions are then detected by the detector 19, pass through the DC amplifier 20 and enter the data processor 21, which in turn provides a mass spectrum.

Figure 4:
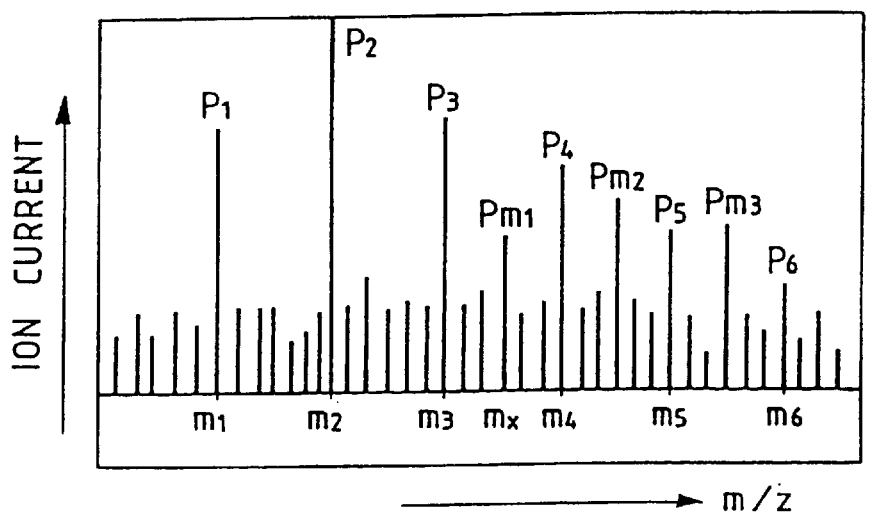
FIG. 4 is a diagram explanatory of chemical noises in a mass spectrum.

Reference will be made below to cluster ions and chemical noise. On the mass spectrum there sometimes appear chemical noises other than ions based on sample. FIG. 4 shows an example of chemical noises appearing on a mass spectrum. Generally, the axis of abscissa of mass spectrum represents mass per charge (m/z) and the axis of ordinate represents ion current. The peaks P1 to P6 appearing at equal intervals on the mass spectrum represent cluster ions. Assuming that the composition of P1 ion is M and with water added thereto, the cluster ions P2 to P6 are represented as $(M+nH_2O)$. In the case of using water as a mobile phase, M is $H_3O$ m/z19. On the mass spectrum, therefore, cluster ions, of water sometimes appear in a large number and with high intensity at every m/z18 like 19, 37, 55 and 73. In some case, water molecule also adds to the sample molecular ion Pm1 and there appear Pm2 and Pm3.

In this case, since one ion species Pm1 is dispensed into several ion species, the ion current value of the molecular ion Pm1 becomes lower. In addition to these ions, ions are detected continuously over a wide mass range. These are presumed to be cluster ions which have reached the detector without accurate mass spectrometric analysis after evaporation of added molecules during flying through the medium pressure chamber 15 and the mass spectrometric analysis portion 18. These ions, except the sample molecular ion Pm1, exert a negative influence on the analysis and obstruct the identification of molecular ion Pm1. The ions in question are generally called chemical noises.

The appearance of such cluster ions can be prevented by conducting the heating of mists to a thorough extent in ionization to make the vaporization of sample or solvent perfect or by heating the whole of the interface. According to the nebulizing means presently used for atmospheric pressure chemical ionization or the like, such as those using gas, heating or ultrasonic wave, mist droplets are distributed widely ranging in diameter, for example, from 100 to 1 $\mu$m. Therefore, if even droplets of large diameters are to be vaporized completely by heating, droplets of smaller diameters undergo heat continuously for a long time after vaporization. Such excess heating causes thermal decomposition of the sample molecules, resulting in loss of all information pieces on the molecular weight and structure of the sample. In this case, it is no longer possible to make analysis as LC/MS.

Thus, cluster ions obstruct the analysis; for example, they obstruct grasping of molecular weight and increase chemical noises. On the other hand, a large number of molecules such as water molecules added to molecules or ions prevent the ambient heat from influencing the molecules or ions directly and thus are effective in preventing thermal decomposition. Further, the applied heat is consumed for the vaporization of added molecules from cluster ions or droplets, thus preventing the rise in temperature of molecules or ions and hence preventing thermal decomposition thereof. Because mist is a droplet-gas mixture, even if mists are heated, the heat is consumed for the vaporization of solvent from the droplet surfaces and therefore the mist temperature does not rise. Consequently, even a thermally unstable substance fed from LC can be fed stably in the state of mists to the atmospheric pressure ion source. Also for this reason, excess heating of the mists must be avoided.

Although a precise temperature control for the heating portion has been tried for the purpose of diminishing chemical noises caused by cluster ions and preventing the thermal decomposition of sample molecules, it is necessary to perform a best point searching operation for each object to be measured and thus the trouble of measurement is enhanced markedly. For liquid chromatography, various methods are available, and a wide variety of solvents are employable, ranging from 100% water to 100% organic solvent for example. Also, putting a salt or an acid into a solvent or using a buffer solution as a mobile phase is conducted frequently. In such a case, it is difficult to control the vaporizer temperature for each mobile phase and for each mobile phase composition, so the application of LC/MS is greatly limited.

Mists can be made uniform by changing the direction of the nebulized jet mechanically so as to stir the marginal flow of a high temperature with the central flow of a relatively low temperature to accelerate the vaporization. By such mechanical change of the nebulized jet direction, the central and marginal flows change places with each other, so that infrared energy radiated from the wall surface of the vaporizing space can be allowed to reach the interior portion of the nebulized jet. On this regard, a detailed description will be given later.

Reference will be made below to the details of the vaporizer 8.

In FIG. 1, the spiral insertion rod 82 serving as a fluid guide is inserted into the vaporizing space 9 which is formed centrally and cylindrically in the vaporizer 8. As a result, the vaporizing space 9 is defined in a spiral form. Mists from the nebulizer 6 (effluent from the chromatography enter the heated, spiral, vaporizing space 9. The mists change the flowing direction thereof continually along the spiral insertion rod. The mist flow is no longer a laminar flow, but its constituent flows come into contact with the heated wall surface continually and are heated thereby. Because the mists are thus agitated and stirred continually, the mist droplets are rendered fine. Thus, the heating is conducted to a sufficient extent and therefore it is possible to set the temperature of the vaporizer 8 low, whereby it is made possible to prevent thermal decomposition of a thermally unstable substance.

Figure 5:
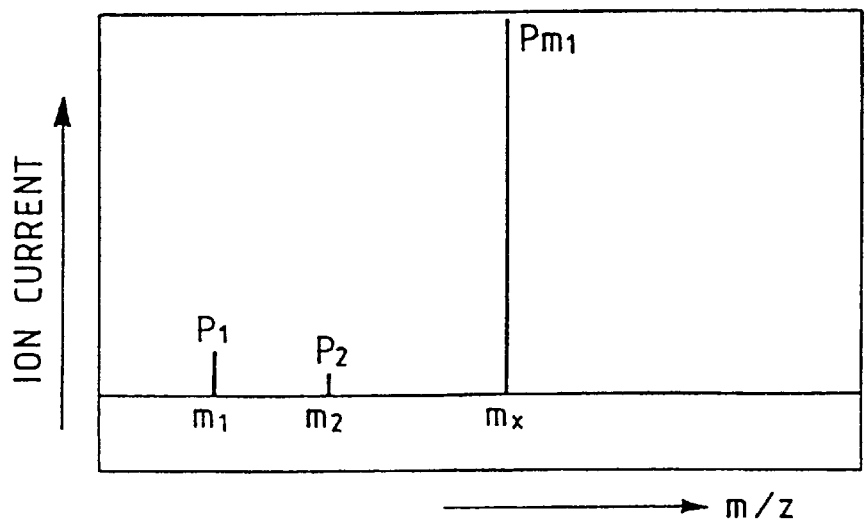
FIG. 5 is a diagram showing a mass spectrum obtained by the present invention.

Uniform and finer mists can be obtained by the adoption of such spiral vaporizing space 9. By introducing the ions of such fine mists into the mass spectrometric analysis portion through the first and second fine holes 14, 16, the desolvation of added molecules is performed efficiently through accelerative collision of the ions in the medium pressure chamber. Further, because it is possible to prevent large-diameter droplets from entering the mass spectrometric analysis portion, chemical noises can be diminished greatly. As a result, such a mass spectrum as shown in FIG. 5 can be obtained. As will be readily seen from the same figure, cluster ions (P1 to P6 in FIG. 4) derived from a mobile phase such as water and chemical noises are extinguished. On the other hand, as to the molecular ions, the ion current value thereof can be increased by splitting off the added molecules because the desolvation of cluster ions proceeds. That is, the ion current values of the peaks Pm1 to Pm3 in FIG. 4 can be aggregated to the peak Pm1. As a result, it becomes possible to identify the molecular ions with high sensitivity.

The vaporizing space 9 can be formed, for example, by drilling the heat block 8 which is made of stainless steel. Then, the spiral insertion rod also made of stainless steel is inserted into the hole thus formed. It is optional whether the spiral is single, double, or more. In place of such spiral insertion rod there may be used a threaded, round rod whose diameter is slightly smaller than the inner periphery of the vaporizing space 9. Preferably, the insertion rod is formed of a thermally conductive material to prevent condensation of the mists. A small-sized heater may be incorporated in the insertion rod, whereby the mists can be heated from the interior and hence the micronization of the mists is accelerated. Further, a freely removable structure of the insertion rod for cleaning purpose permits the prevention of contamination, etc.

The following description is now provided about LC/MS according to the second embodiment of the present invention.

Figure 6A:
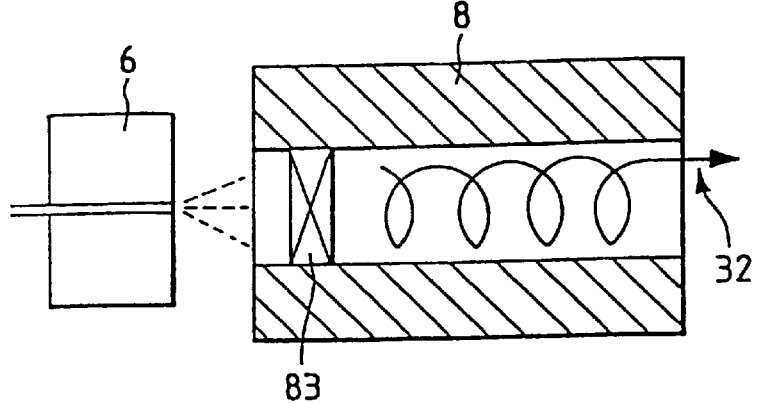
FIGS. 6(a) and (b) are diagrams showing the details of a vaporizer used in embodiment 2 of the invention.
Figure 6B:
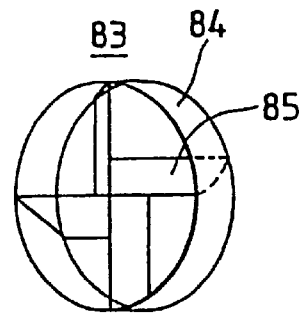

FIGS. 6(a) and (b) are explanatory diagrams of a vaporizer 8 portion in LC/MC according to this second embodiment. Other portions are the same as in the first embodiment so explanations thereof are here omitted. In this embodiment, moreover, the nebulization of a sample solution, introduction of the nebulized jet into the vaporizer 8 and introduction of ions into the MS portion 18 after ionization in the atmospheric pressure chemical ion source 11 are the same as in the first embodiment. FIG. 6(a) is a sectional view of the vaporizer 8. In the first embodiment a spiral insertion rod is inserted into the whole of the vaporizing space 9, while in this embodiment a fluid guide 83 is placed in part of a vaporizing space 9 formed centrally of the vaporizer 8, as shown in FIG. 6(a). The fluid guide 83 comprises a plurality of propeller-like fins 85 which are twisted with respect to each other and a cylinder 84 which fixes those fins. Mists from the nebulizer 6 form a spiral flow in the vaporizing space 9 under the action of the fins 85, whereby there is attained uniform heating and the mists are made fine. Two or more fluid guides 83 may be disposed within the vaporizing space 9.

Reference will be made below to LC/MS according to the third embodiment of the present invention.

Figure 7A:
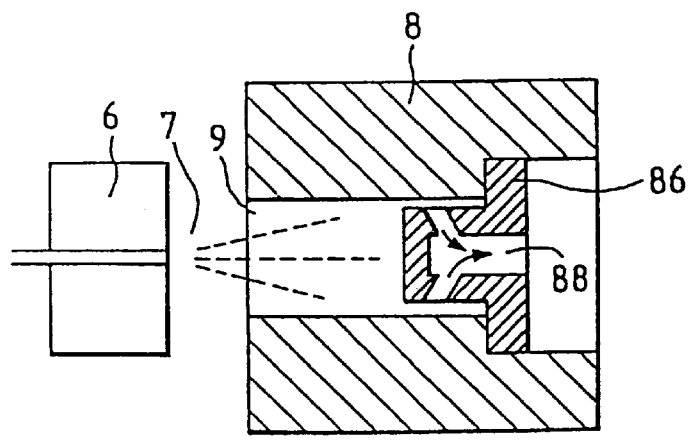
FIGS. 7(a) and (b) are diagrams showing the details of a vaporizer used in embodiment 3 of the invention.
Figure 7B:
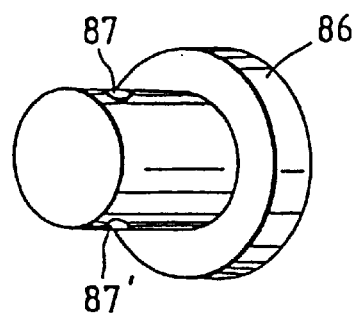

FIGS. 7(a) and (b) are explanatory diagrams of a vaporizer 8 portion in LC/MS according to this embodiment 3. FIG. 7(a) is a sectional view of the vaporizer 8. In this embodiment, nebulization of a sample solution, introduction of the nebulized jet into the vaporizer 8 and introduction of ions into the MS portion 18 after ionization in the atmospheric pressure chemical ion source 11 are the same as in the previous embodiment. As shown in FIG. 7(a), a stirrer 86 having a central hole which serves as a stirring portion 88 is placed within a vaporizing space 9. Plural inlet holes 87 are formed in the outer periphery of the stirrer 86 so as to communicate with the hole of the stirring portion 88.

Mists from the nebulizer 6 enter the vaporizing space 9 and are heated thereby. The marginal flow of the mists, which flow is heated well, immediately passes through the inlet holes 87 formed in the outer periphery of the stirrer 86 and reaches the stirring portion 88, while the central flow of the mists moves along the wall surface of the stirrer 86 and reaches the stirring portion 88 through the inlet holes 87. Thus, the central flow low in temperature can be heated while moving slowly near the inner peripheral portion of the vaporizer 8. Further, by stirring in the stirrer 88, uniform heating is attained and the mists are rendered fine. The structure of the stirrer 86 is not limited to the illustrated one. Other shapes may be adopted if only marginal and central flows are taken in separately and then stirred in a single place.

If the stirrer 86 is formed so that it can be inserted from the exterior into the vaporizing space 9 and can be removed therefrom, it becomes possible to conduct cleaning easily.

LC/MS according to a the fourth embodiment of the present invention will be described below.

Figure 8:
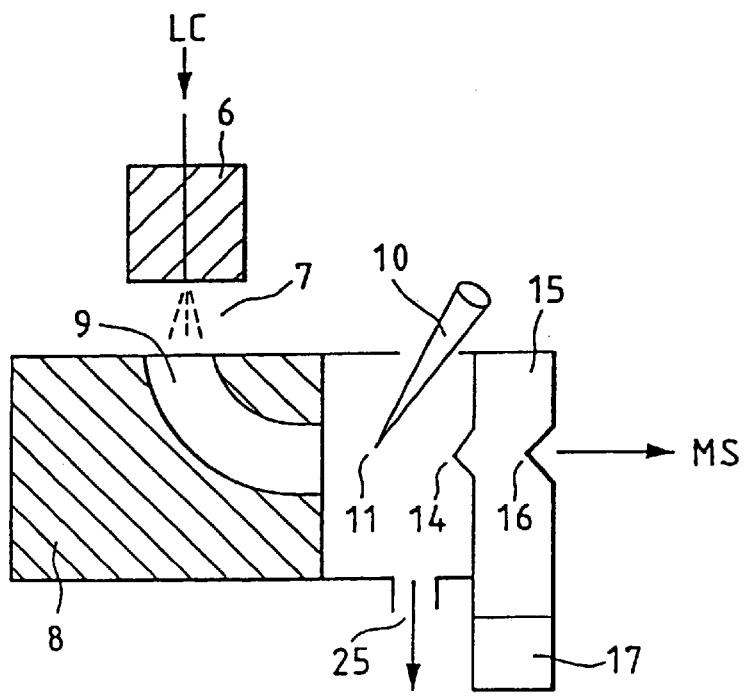
FIG. 8 is a diagram showing the details of LC/MS according to embodiment 4 of the invention.

FIG. 8 is an explanatory diagram of a vaporizer 8 portion used in the LC/MS of this embodiment. In this embodiment, nebulization of a sample solution, introduction of the nebulized jet into the vaporizer 8 and introduction of ions into the MS portion 18 after ionization in the atmospheric pressure ion source 11 are the same as in the previous embodiments. FIG. 8 is a sectional view of the nebulizer 8. In this embodiment, a bent vaporizing space 9 is formed in the interior of the vaporizer 8. Mists from the nebulizer 6 enter the vaporizing space 9 which is heated. The mists change the flowing direction thereof along the bent vaporizing space 9. The mists undergo a force in a direction different from its advancing direction, so that the marginal and central flows which constitute the mists change places with each other and are heated in proximity to the heated wall surface, whereby the mists can be heated uniformly and hence the micronization of the mists can be attained.

Figure 9:
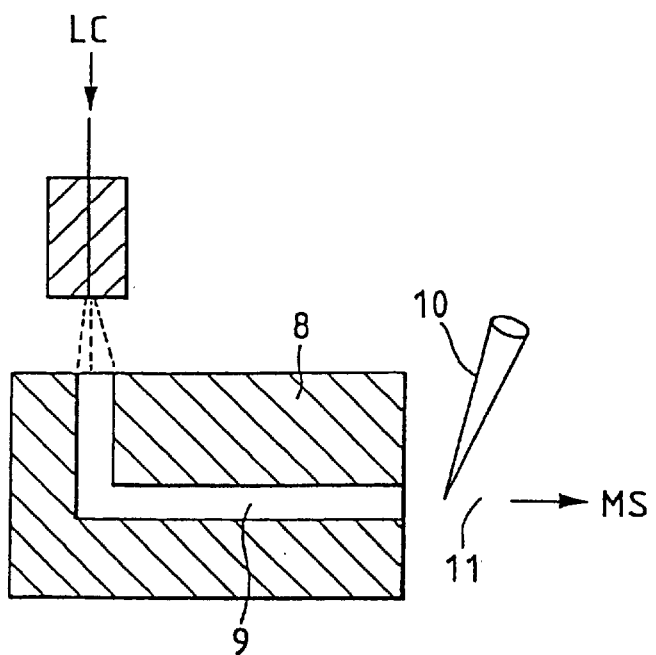
FIG. 9 is a diagram showing the details of a vaporizer used in embodiment 4.
Figure 10:
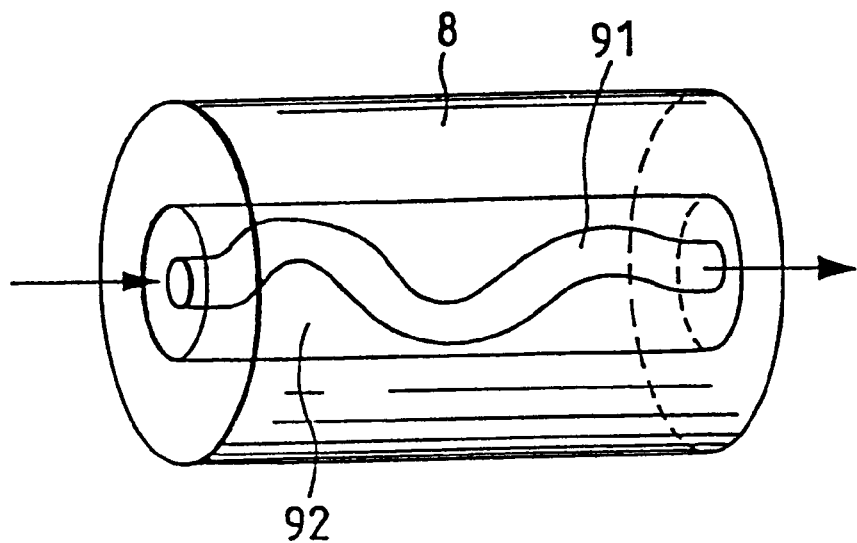
FIG. 10 is a diagram showing the details of a vaporizer employable in embodiment 4.

Although the vaporizing space in FIG. 8 is formed at an angle of 90°, there may be adopted another angle. There may be formed a vaporizing space 9 perpendicular to the vaporizer 8, as shown in FIG. 9. A plurality of bent vaporizing spaces may be combined together. Further, a curved vaporizing space 9 can be formed by curving a metallic tube, then inserting the curved tube into a hole formed in the block of the vaporizer 8 and thereafter welding the tube to the block using silver solder 92 or the like, as shown in FIG. 10.

Figure 11:
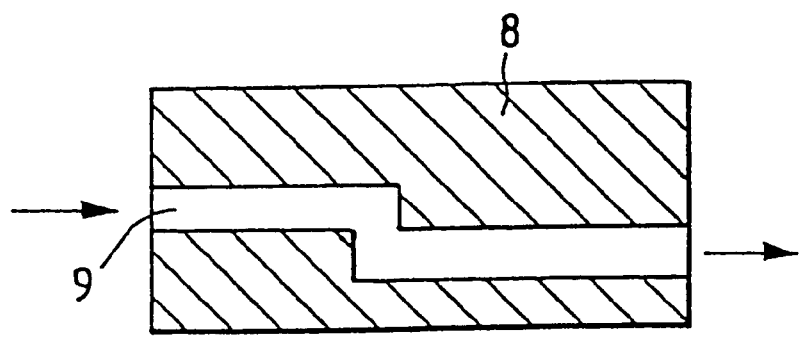
FIG. 11 is a diagram showing the details of a vaporizer employable in embodiment 4.

Moreover, two holes of different axes may be formed within the block of the vaporizer 8 and then interconnected within the block, as shown in FIG. 11. Further, two or more vaporizer blocks having holes respectively may be mounted together so that the axes of the holes are displaced from each other.

Figure 12:
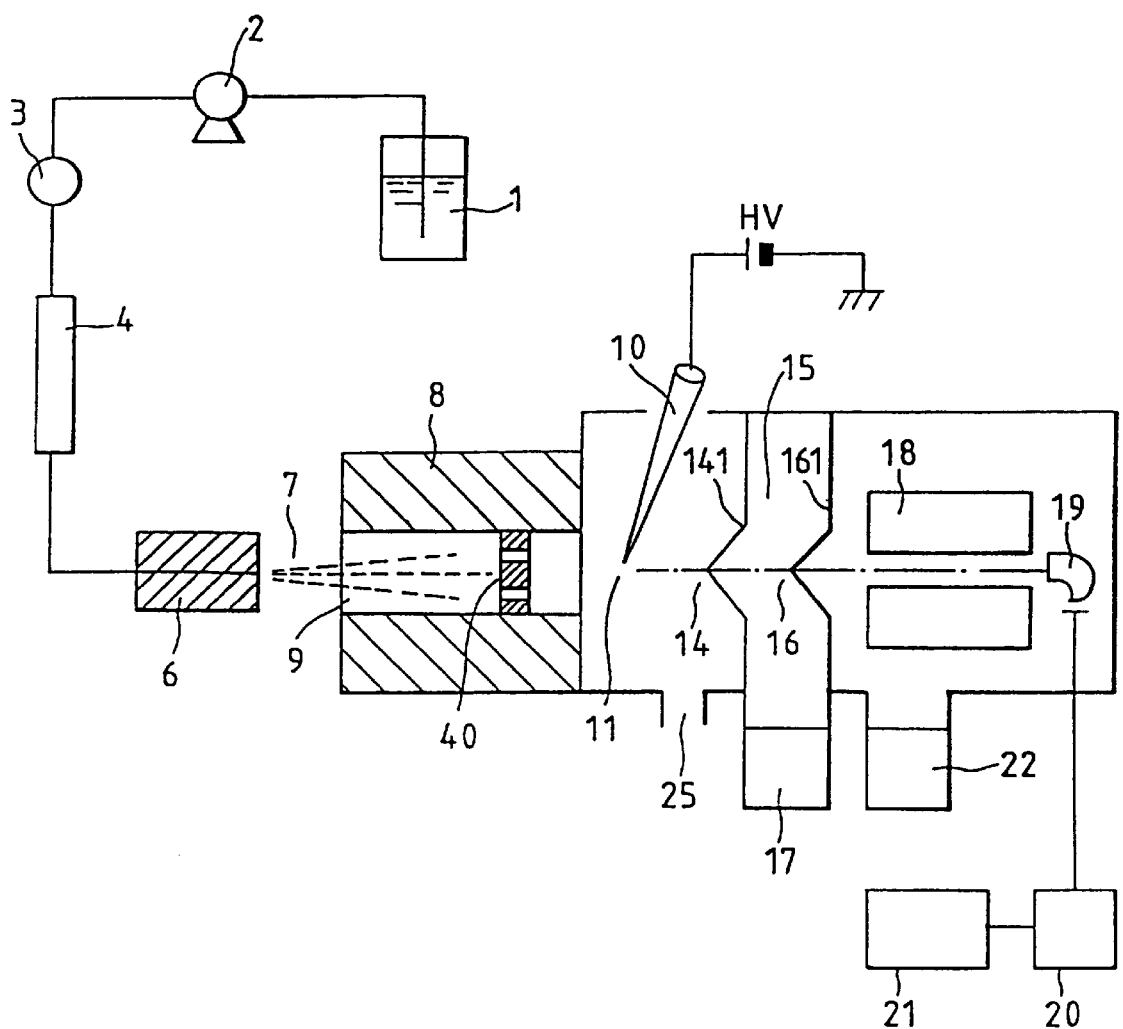
FIG. 12 is a diagram showing the details of a vaporizer used in embodiment 5 of the invention.
Figure 13A:
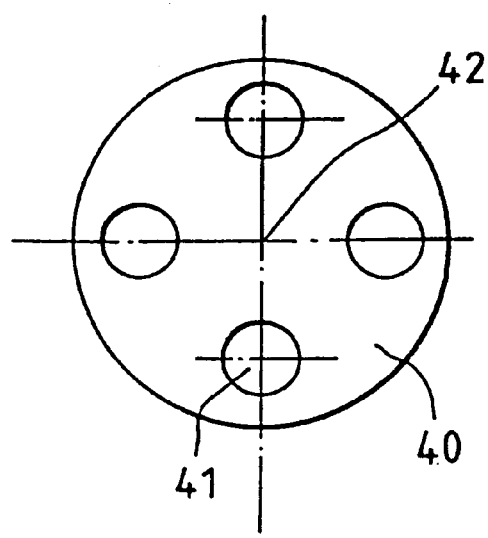
FIG. 13 is a diagram showing the details of a turbulent flow generating plate used in embodiment 5.
Figure 13B:
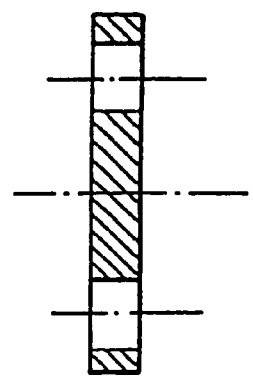

FIG. 12 is an explanatory diagram showing LC/MS (incl. interface) according to the fifth embodiment of the present invention, and FIG. 13 illustrates a turbulent flow generating plate. In this embodiment, nebulization of a sample solution, introduction of the nebulized jet into the vaporizer 8 and introduction of ions into the MS portion 18 after ionization in the atmospheric pressure ion source 11 are the same as in the previous embodiments.

Figure 14:
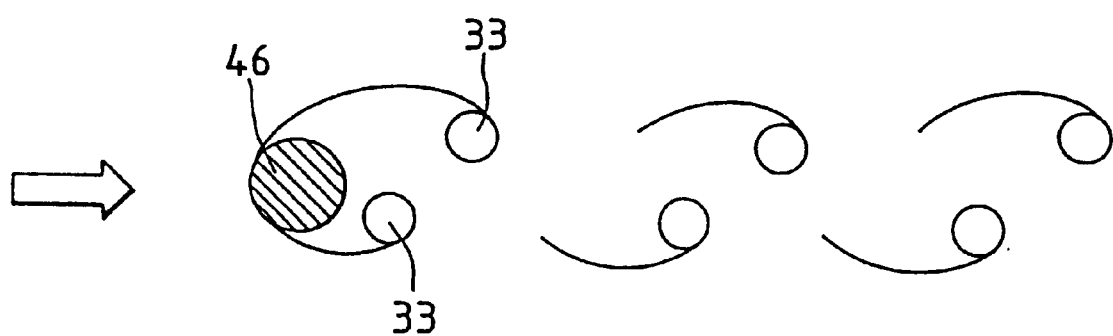
FIG. 14 is a diagram explaining how Kármán's vortex is created in embodiment 5.

Reference will be made first to a basic function of the turbulent flow generating plate. As shown in FIG. 14, if an object 46 is placed within a fluid, a negative pressure is developed behind the object 46. To compensate for this point, the fluid moves curvilinearly from the outside behind the object 46 to form tapping vortexes one after another on both sides. These vortexes are known as Kármán's vortexes. By utilizing these vortexes it is made possible to stir the mists and thereby render the mists fine.

Figure 15:
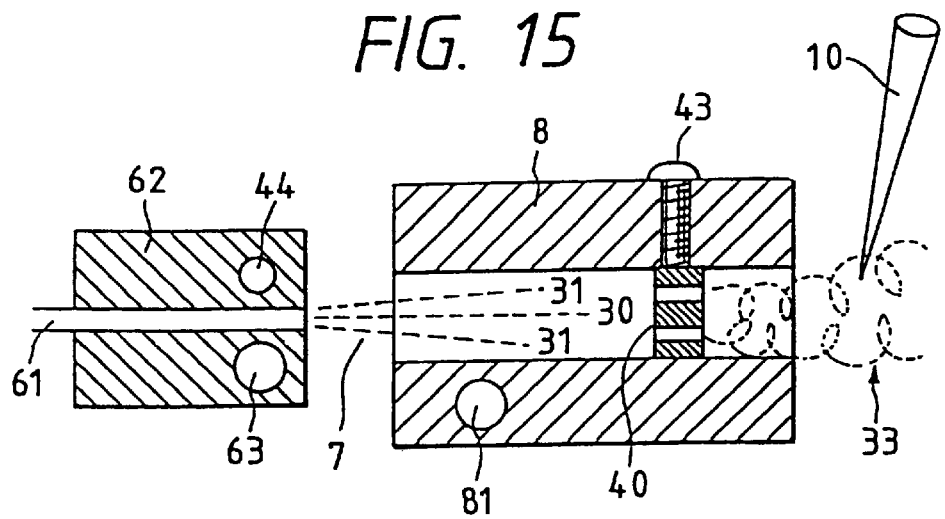
FIG. 15 is a diagram showing the details of nebulization in embodiment 5.

More specifically, a turbulent flow generating plate 40 is placed in a vaporizing space 9, as shown in FIGS. 12 and 15. The turbulent flow generating plate 40 has such a structure as shown in FIG. 13. A plurality of small through holes 41 are formed on a certain circumference from a central point 42 of the vaporizing space 9. For example, the turbulent flow generating plate 40 may be a stainless steel disk having a thickness of about 1 to 5 mm. In the presence of the turbulent flow generating plate 40 placed within the vaporizing space 9, mists are once obstructed by the plate 40, then pass through the aforesaid plural through holes and form turbulent flows (vortexes) in the downstream direction. The flow rate of the solution fed to the nebulizer 6 is, say, 1 ml/min or so, and after vaporization, it becomes, say, 1,000 ml/min. Such a large flow rate of gas (mists) passes through the vaporizing space 9 which is, say, several millimeters in inside diameter and 50 mm or so in length, so that fine droplets get on the flow of vaporized solvent and pass through the through holes 41 without collision with the turbulent flow generating plate 40. The flow which has passed the through holes 41 forms turbulent flows (vortexes) 32 downstream of the turbulent flow generating plate 40. The marginal flow 31 containing fine droplets of high temperature and the central flow 30 containing large droplets of low temperature are agitated mechanically by virtue of the turbulent flows 32. As a result, the temperature of the nebulized jet can be rendered uniform and the vaporization of large droplets is accelerated. Moreover, large droplets are torn mechanically by a complicated gas flow and thus the micronization of the mists is further promoted. In this way the mists are rendered fine and uniform upon passing through the turbulent flow generating plate 40. Further, the mists thus micronized through the vaporizer 8 then enter the atmospheric pressure ion source 11 and are ionized therein.

The vaporizing space 9 can be formed easily by forming a hole circular in section and having a diameter of 5 mm and a length of 50 mm in the heat block 8 of stainless steel. The turbulent flow generating plate 40 may be disposed in a position about 40 mm from the inlet of the vaporizing space 9. For the prevention of stain, the turbulent flow generating plate 40 is formed of a material superior in thermal conductivity so as to be maintained at approximately the same temperature as that of the vaporizer 8. As shown in FIG. 15, the turbulent flow generating plate 40 is fixed to the vaporizer 8 with a fixing bolt 43 so that it can be removed and washed when stained after repeated measurement.

LC/MS according to the sixth embodiment of the present invention will be described below.

Figure 16A:
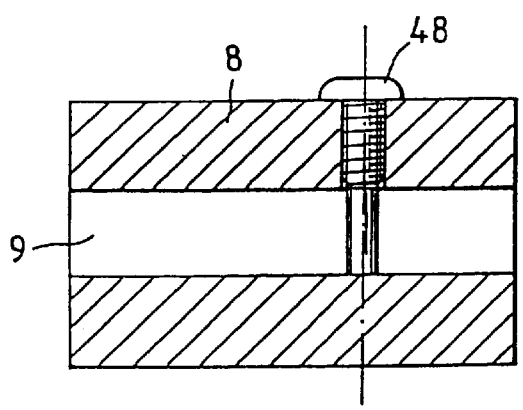
FIG. 16 is a diagram showing the details of a vaporizer used in embodiment 6 of the invention.
Figure 16B:
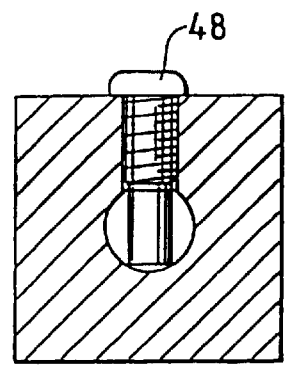

FIG. 16 is an explanatory diagram of a vaporizer 8 portion used in the LC/MS of this embodiment. In this embodiment, nebulization of a sample solution, introduction of the nebulized jet into the vaporizer 8 and introduction of ions into the MS portion 18 after ionization in the atmospheric pressure ion source 11 are the same as in the previous embodiments.

In this embodiment, a hole is formed in the vaporizer 8 in a position downstream of a vaporizing space 9 and a bolt 48 is inserted into the hole. The bolt 48 has a length sufficient to reach the wall surface on the lower side of the vaporizing space 9. The diameter of the bolt 43 is smaller than that of the vaporizing space 9 so that there is a sufficient clearance in the space 9 even when the bolt 43 is tightened completely. Mists enter the vaporizing space 9 and are heated by infrared energy radiated from the wall surface of the vaporizer 8. The mists thus heated by-passes the bolt 48 and form turbulent flows (vortexes) downstream of the bolt 48. As to the principle of turbulent flow formation, it is shown in FIG. 14. By the formation of such turbulent flows (vortexes) there are attained micronization and uniforming of the mists as in embodiment 5. The bolt 48 is formed of a material superior in thermal conductivity to prevent the condensation of solvent and sample. Positioning of the bolt 48 can be done easily from the exterior using a screw-driver or the like, whereby the flow of the mists can be controlled freely. Consequently, it is possible to easily find out a point most effective for the micronization of the mists. The bolt 48, when stained, can be easily removed for cleaning.

LC/MS according to the seventh embodiment of the present invention will be described below.

Figure 17:
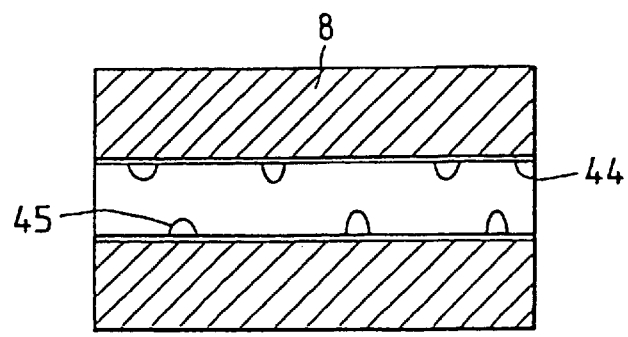
FIG. 17 is a diagram showing the details of a vaporizer used in embodiment 7 of the invention.

FIG. 17 is an explanatory diagram of a vaporizer 8 portion used in the LC/MS of this embodiment. In this embodiment, nebulization of a sample solution, introduction of the nebulized jet into the vaporizer 8 and introduction of ions into the MS portion after ionization in the atmospheric pressure ion source 11 are the same as in embodiment 1.

According to this embodiment, a plurality of projections 45 are formed on the wall surface of a cylindrical vaporizing space 9 formed centrally through the vaporizer 8. The mists which have entered the vaporizing space 9 by-pass the projections 45 and form a large number of turbulent flows (vortexes) behind the projections 45. By the formation of such turbulent flows there are attained micronization and uniforming of the mists. In place of forming the projections 45 directly on the wall surface of the cylindrical vaporizing space 9 there may be used a separate cylindrical tube 44 having the projections 45 in the interior thereof and capable of being inserted into the space 9. The cylindrical tube 44 can be removed and washed when stained.

Thus, according to first through seventh embodiments, there are performed micronization and uniforming of mists in the vaporizing space to prevent mists irregular in droplet diameter from being introduced in a disorderly manner into the atmospheric pressure ion source; in other words, fine droplets uniform in diameter can be ionized and introduced into the MS portion, thus permitting desolvation to be performed efficiently. As a result, the generation of chemical noises can be kept to a minimum and it is possible to attain highly sensitive analysis. It is also made possible to select a suitable solvent out of various composition.

LC/MS according to a the eighth embodiment of the present invention will be described below.

Figure 18A:
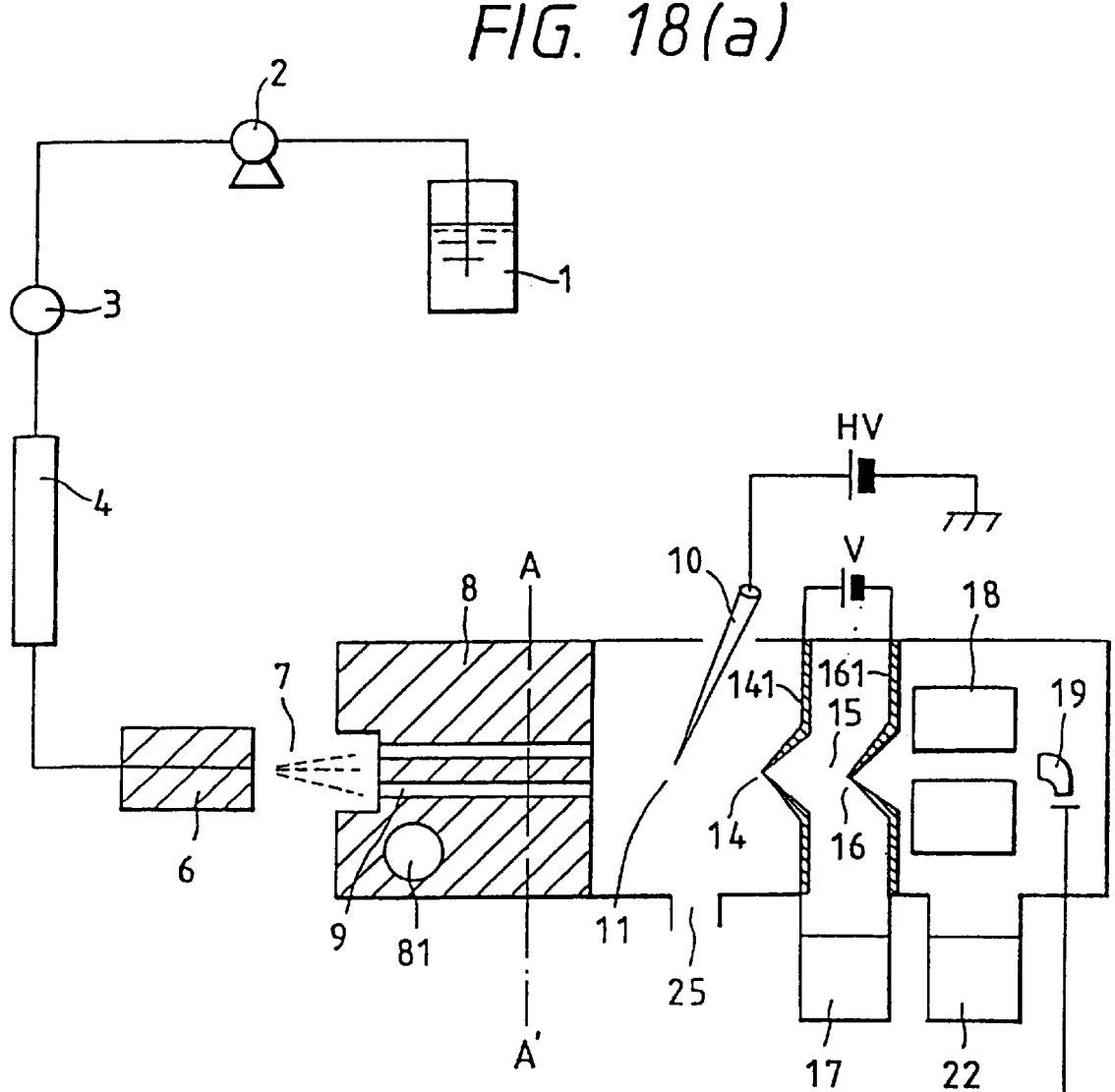
FIGS. 18(a) and (b) are diagrams showing the whole of LC/MS according to embodiment 8 of the invention.
Figure 18B:
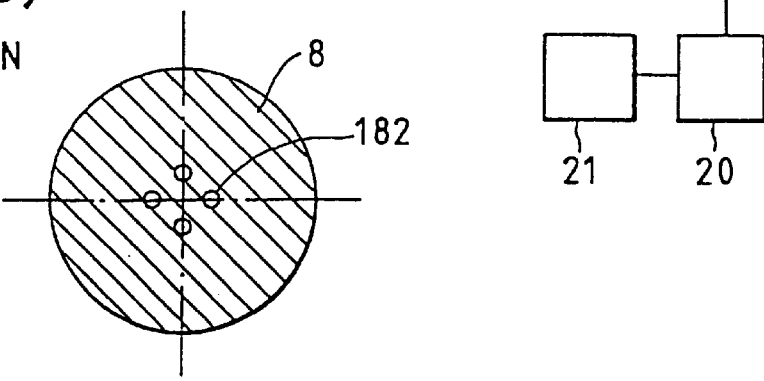
Figure 19:
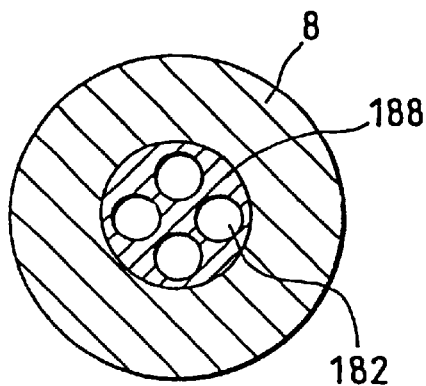
FIG. 19 is a diagram showing the details of a vaporizer used in embodiment 8.

Mists can be made uniform by dividing a nebulized jet mechanically into flows smaller in diameter so that infrared energy radiated from the wall surface of a vaporizing space reaches the interior of the nebulized jet. In this embodiment, as shown in FIG. 18, a plurality of vaporizing spaces 9, for example a plurality of fine tubes 182 are provided within the extent of mists from the central portion of a vaporizing space 8. The mists are divided and pass separately through the plural fine tubes 182 which are heated. Inevitably the diameter of each mist is restricted to a value not larger than the diameter of each fine tube 182. Because of increase in the surface area of the fine tubes 182, infrared energy radiated from the wall surfaces of the fine tubes increases so much and therefore each mist can be heated easily up to the central part thereof. In this way the micronization of mists proceeds. In the case where the mist flow diameter is large, it is difficult for the heat to reach the central part of each mist, and it is required to set high the temperature of the vaporizer 8 to attain heating up to the central part of each mist. But in this embodiment, the temperature of the vaporizer 8 can be set low because heating is conducted sufficiently. As a result, it is possible to prevent thermal decomposition of a thermally unstable substance. The mists which have passed through the plural fine tubes 182 enter the atmospheric pressure ion source 11, in which the solvent particles are first ionized by corona discharge generated from the tip of the needle electrode for corona discharge with a high voltage of 3 to 5 kV applied thereto. The resulting ions then repeat ion-molecule reaction and eventually ionize the sample molecules. The ions are introduced through the first fine hole 14 into the medium pressure portion 15. This point is the same as in the previous embodiments.

Thus, by the adoption of plural vaporizing spaces 9 it is possible to obtain fine mists. The mists are then ionized and the resulting ions can be introduced through first and second fine holes 14, 16 into the mass spectrometric analysis portion 18. The fine droplets are subjected to accelerative collision of ions in the medium pressure chamber, whereby the desolvation of added molecules is performed efficiently. Further, because it is possible to prevent droplets of large diameters or cluster ions from being introduced into the mass spectrometric analysis portion, the generation of chemical noises can be decreased greatly. It is also possible to minimize the formation of cluster ions derived from a mobile phase such as water and the resulting chemical noise. On the other hand, as to molecular ions, their ion current value can be increased by stripping off the added molecules. As a result, it becomes possible to identify molecular ions with high sensitivity. The vaporizing spaces 9 can be formed by drilling the vaporizer, or a heat block, 8 formed of stainless steel.

LC/MS according to the ninth embodiment of the present invention will be described below.

Figure 20:
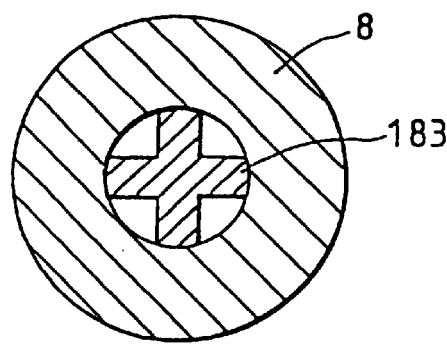
FIG. 20 is a diagram showing the details of a vaporizer used in embodiment 9 of the invention.

FIG. 20 is an explanatory diagram of a vaporizer 8 portion used in the LC/MS of this embodiment. In this embodiment, nebulization of a sample solution, introduction of the nebulized jet into the vaporizer 8 and introduction of ions into the MS portion 18 after ionization in the atmospheric pressure ion source 11 are the same as in the previous embodiments. The vaporizer 8 is shown as a sectional view in FIG. 20. A hole about 5 mm in diameter by 50 mm in length is formed centrally of the vaporizer 8, and a rod-like partition plate 183 is inserted into the hole. Although the partition plate shown in FIG. 20 is cross-shaped, it is possible to select a desired shape of the partition plate 183 freely. By the insertion of such partition plate into the hole, a vaporizing space 9 is divided into plural vaporizing spaces so that mists can move through each vaporizing space. According to this embodiment, like the eighth, there are attained subdivision of mist flow and increase in the number of heating wall surfaces. As a result, the vaporization of mist droplets is promoted and the mists are rendered fine. The partition plate 183 is formed of a material superior in thermal conductivity, whereby the heating of mists is effected to a satisfactory extent and therefore the condensation of sample can be prevented. Moreover, if a small-sized heater is incorporated in the partition plate 183, the mists can be heated from the interior, so that the micronization of the mists is accelerated. Further, if the vaporizer is designed so that the partition plate 183 can be removed to the exterior, cleaning of the partition plate can be done easily.

LC/MS according to the tenth embodiment of the present invention will be described below.

Figure 21:
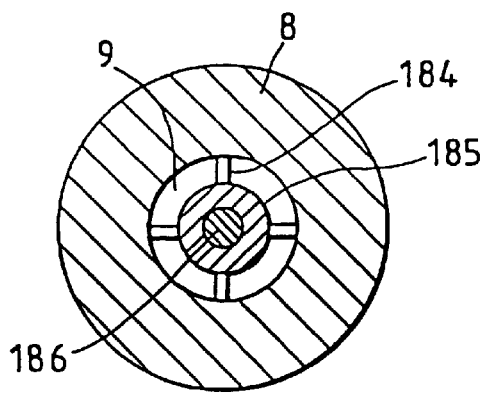
FIG. 21 is a diagram showing the details of a vaporizer used in embodiment 10 of the invention.

FIG. 21 is an explanatory diagram of a vaporizer 8 portion used in the LC/MS of this embodiment. In this embodiment, nebulization of a sample solution, introduction of the nebulized jet into the vaporizer 8 and introduction of ions into the MS portion 18 after ionization in the atmospheric pressure ion source 11 are the same as in the previous embodiments. The vaporizer is shown as a sectional view in FIG. 21. A hole having, say, a diameter of 5 mm and a length of 50 mm is formed centrally through the vaporizer 8. An insertion rod 185 having a plurality of projections 184 on the outer periphery thereof is inserted into the hole, whereby vaporizing spaces 9 are formed in the gaps defined by outer peripheral portions of the insertion rod 185 and inner peripheral portions of the hole formed in the vaporizer 8. A suitable thickness of each vaporizing space 9 can be set freely by changing the diameter of the insertion rod. If the vaporizing space thickness is set as small as 1 mm or so, it will be possible to heat the mists to a satisfactory extent. And if the vaporizer is designed so that the insertion rod 185 can be taken out to the exterior, cleaning of the insertion rod can be done easily. Further, if a small-sized heater 186 is sealed into the insertion rod 185 so as to conduct heating from the interior, the micronization of mists is further accelerated.

LC/MS according to the eleventh embodiment of the present invention will be described below.

Figure 22:
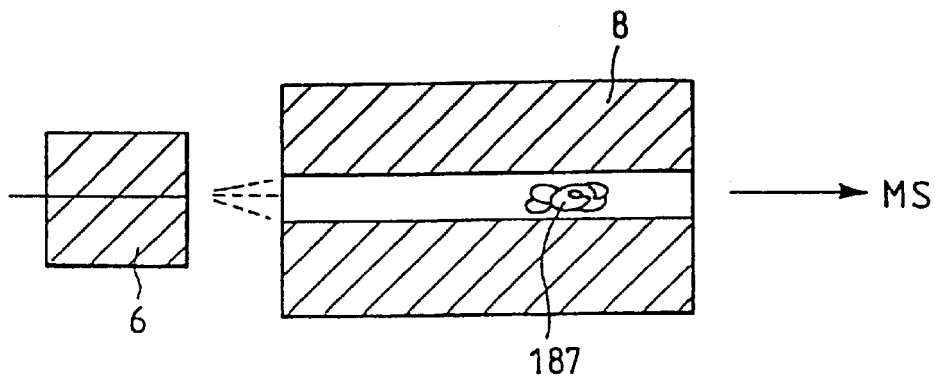
FIG. 22 is a diagram showing the details of a vaporizer used in embodiment 11 of the invention.

FIG. 22 is an explanatory diagram of a vaporizer 8 portion used in the LC/MS of this embodiment. In this embodiment, nebulization of a sample solution, introduction of the nebulized jet into the vaporizer 8 and introduction of ions into the MS portion 18 after ionization in the atmospheric pressure ion source 11 are the same as in the previous embodiments. In FIG. 22, the vaporizer 8 is shown as a sectional view taken in the nebulizing direction. A hole having, say, a diameter of 5 mm and a length of 50 mm is formed centrally through the vaporizer 8. Then, in the hole thus formed, which serves as a vaporizing space 9, is placed a packing 187 such as quartz wool or stainless steel wool. When the mists after entry into the vaporizing space 9 has reached the packing 187, a plurality of flows are formed, which are subjected to heating from the wall surface of the vaporizer 9. As a result, the micronization of the mists is further accelerated.

According to the eighth to eleventh embodiments, as set forth above, it is possible to prevent mists irregular in droplet diameter from being introduced in a disorderly manner into the atmospheric pressure ion source 11, and because the temperature is made uniform, it is possible to ionize fine droplets which are uniform in diameter and then introduce the resulting ions into the MS portion. Consequently, desolvation can be done efficiently at an ion drift voltage V, and hence it is possible to keep the generation of chemical noise to a minimum and attain highly sensitive analysis. Further, the temperature of the vaporizer can be set low and it is possible to prevent the thermal decomposition of a thermally unstable substance.

Figure 23:
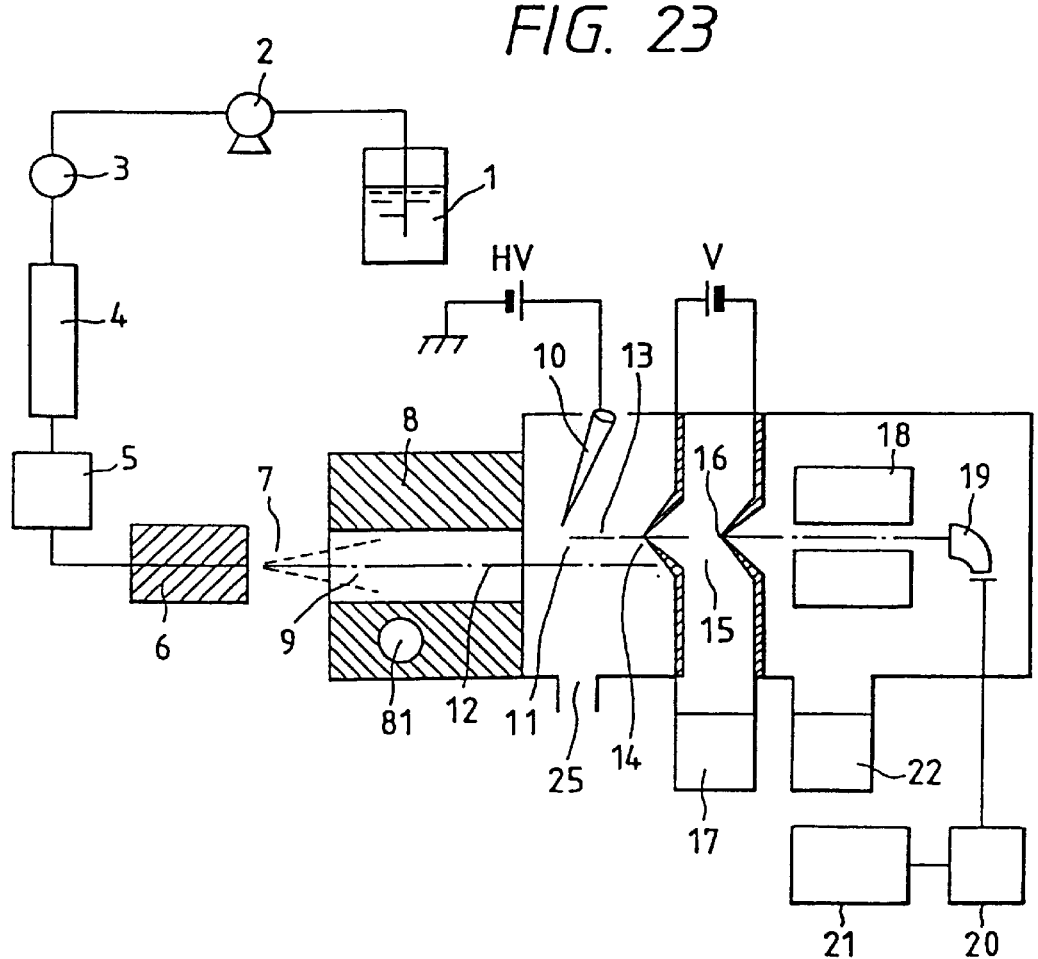
FIG. 23 is a diagram showing the whole of LC/MS according to embodiment 12 of the invention.
Figure 24:
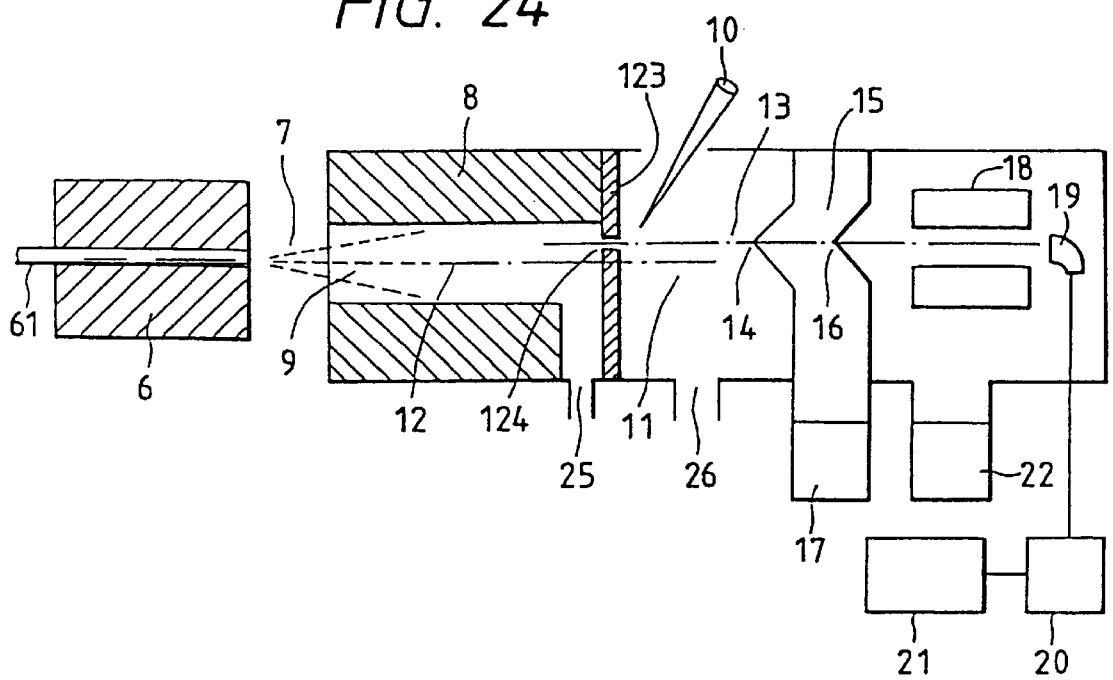
FIG. 24 is a diagram showing the whole of LC/MS according to embodiment 13 of the invention.

FIG. 23 is a diagram explanatory of LC/MS (incl. interface) according to the twelfth embodiment of the present invention. FIG. 24 is an enlarged diagram of a nebulizer portion and a vaporizer portion.

In FIGS. 23 and 24, an ion sampling axis 13 is set in a position near a marginal flow 31 of mists, whereby it is made possible to ionize mainly fine mists and introduce the resulting ions into the mass spectrometric analysis portion 18 through first and second fine holes 14, 16. That is, because a large number of fine mists gather in the marginal portion of nebulized mists, those fine mists are selected qualitatively and conducted into the medium pressure chamber 15. Further, the ions from fine droplets repeat accelerative collision under the application of an ion drift voltage V between both partition walls 141 and 161, whereby the desolvation of added molecules is performed efficiently. Moreover, because large-diameter droplets present in the central flow of mists can be prevented from being introduced into the mass spectrometric analysis portion, it is possible to greatly reduce chemical noise. Consequently, it is possible to suppress the formation of cluster ions derived from a mobile phase such as water and the resulting chemical noise. On the other hand, as to molecular ions, their ion current value can be increased by removing the added molecules. As a result, it becomes possible to identify molecular ions with high sensitivity.

LC/MS according to the thirteenth embodiment of the present invention will be described below.

FIG. 24 is an explanatory diagram of the LC/MS of this embodiment, in which the same reference numerals as in FIGS. 22 and 23 represent equivalent portions and therefore the explanation thereof is here omitted. Only the portions indicated by new reference numerals will be explained below.

In FIG. 24, the reference numeral 123 denotes a partition wall, numeral 124 denotes a nebulized jet sampling hole, numeral 25 denotes a first discharge port and numeral 26 denotes a second discharge port. In this embodiment, the operations up to the nebulization of a sample solution and introduction of the nebulized jet into the vaporizer 8 are the same as in the previous embodiments. A partition wall 123 having a hole 124 is disposed downstream of a vaporizing space 9 and in front of the atmospheric pressure ion source 11. The vaporizing space 9 and the atmospheric ion source 11 are isolated from each other by the partition wall 123. The hole 124, which is a fine hole, is formed in a position deviated from the central axis 30 of the nebulized jet and near the marginal flow 31. Fine mists are concentrated on the marginal portion in comparison with the central portion, whereby the marginal mists in the nebulized jet can be selectively introduced and ionized in the atmospheric pressure ion source 11. The mists contained in the nebulized jet but not introduced into the ion source 11 are discharged to the exterior through the first discharge port 25, and the gaseous portion which has not participated in the ionization after introduction into the atmospheric pressure ion source 11 is discharged to the exterior through the second discharge port 26. In the case of the first embodiment there is the likelihood of droplets different in diameter being mixed due to turbulent flows formed within the ion source and being introduced into the mass spectrometric analysis portion. According to the second embodiment, however, because only the mists present in the marginal portion of the nebulized jet are sampled positively, it is possible to ionize fine mists of uniform diameter selectively. Such uniform, fine ions undergo accelerative collision under the application of an ion drift voltage V in the medium pressure chamber, with the result that the desolvation is performed efficiently.

Although in the above description of this embodiment the partition wall 123 with hole 124 is fixed within the apparatus, it is also possible to make such partition wall 123 adjustable from the exterior in a direction perpendicular to the nebulized jet, whereby sampling of the nebulized jet can be done freely and it becomes possible to sample and ionize a desired diameter of droplets. Such adjustment from the exterior makes it possible to find out a best point corresponding to maximum sensitivity and minimum noise.

Although in the twelfth and thirteenth embodiments the sampling method for ions produced under atmospheric pressure has been described using a fine hole, there is made no limitation to such fine hole, which may be substituted by, for example, slit or capillary if only the ions formed can be introduced into the MS portion while maintaining a pressure difference. The mass spectrometer is not limited to QMS, either; it may be a sector-type MS, an ion trap type MS, or an MS based on a different principle.

According to embodiments the twelfth and thirteenth, as described above, mists of droplets uniform in diameter can be ionized and then fed into the MS portion while mists of droplets irregular in diameter are prevented from being introduced in a disorderly manner into the atmospheric pressure ion source, and thus the desolvation can be done efficiently, whereby it is made possible to minimize the generation of chemical noise and attain highly sensitive analysis.

The following experiment has been conducted for the purpose of demonstrating the effects of the present invention.

(1) Apparatus

LC/MS having the construction shown in FIG. 12 was used, provided the analyzing column 4 was removed and the sample inlet 3 and the nebulizer 6 were directly connected with each other. Comparison was made between the case where the turbulent flow generating plate 40 was used and the case where it was removed.

Pure water was used as the mobile phase 1. Water is most difficult to be desolvated and forms large cluster ions. The vaporizer temperature was set to 400° C. and the degree of development of cluster ions was observed while changing the temperature of the nebulizer 6 and the flow rate of water. Corona discharge voltage HV was set at 3 kV, the drift voltage V for collision-induced dissociation was set at 50V, and other parameters were fixed during the experiment. Mass spectra were collected repetitively by sweeping the mass spectrometer 18 while changing the temperature of the nebulizer 6 and the flow rate of water. Cluster ions on each mass spectrum are integrated and outputted as total ion current (TIC). A large value of TIC indicates that a large number of cluster ions are developed. It can be said herein that TIC and chemical noise are synonyms.

(2) Results and Study

Figure 25:
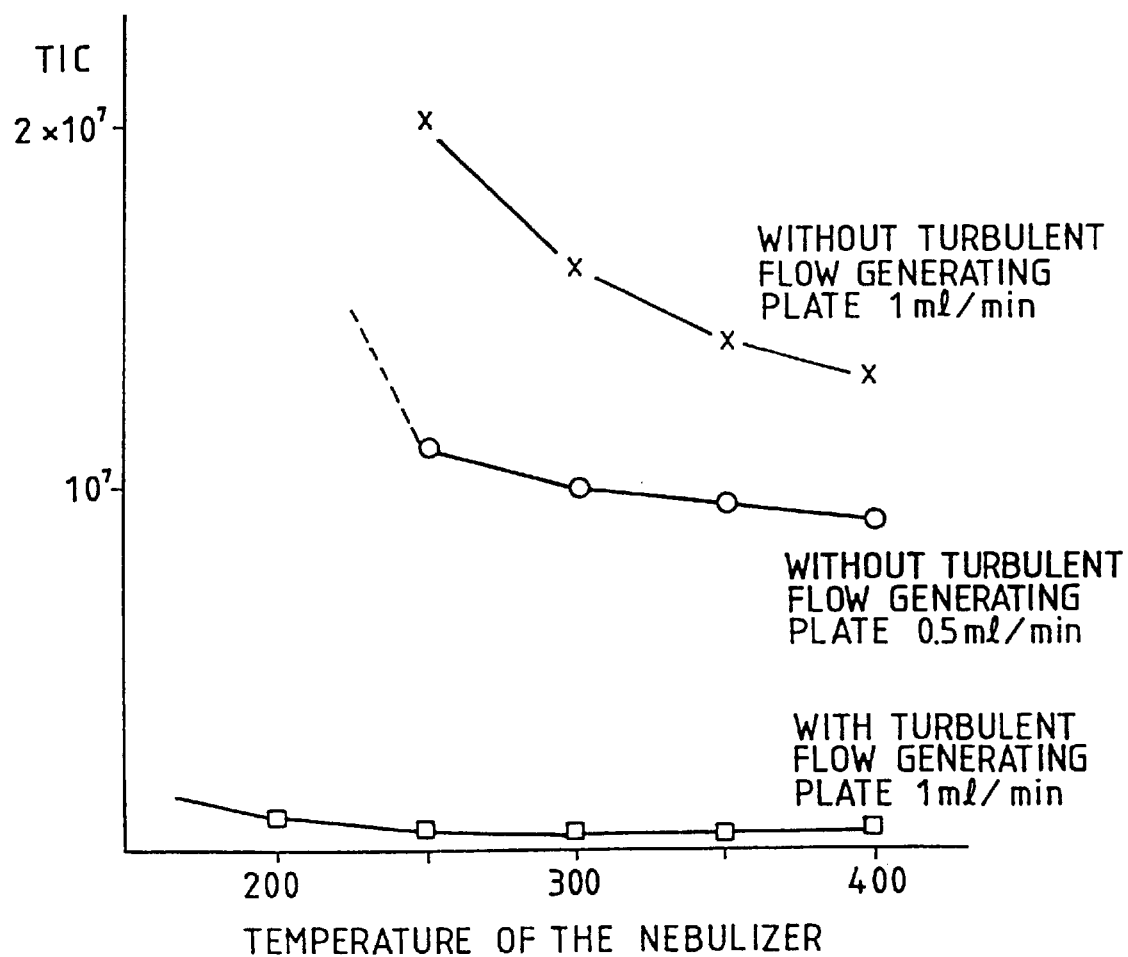
FIG. 25 is a diagram showing a relation between total ion current (TIC) and the temperature of a nebulizer.
Figure 26A:
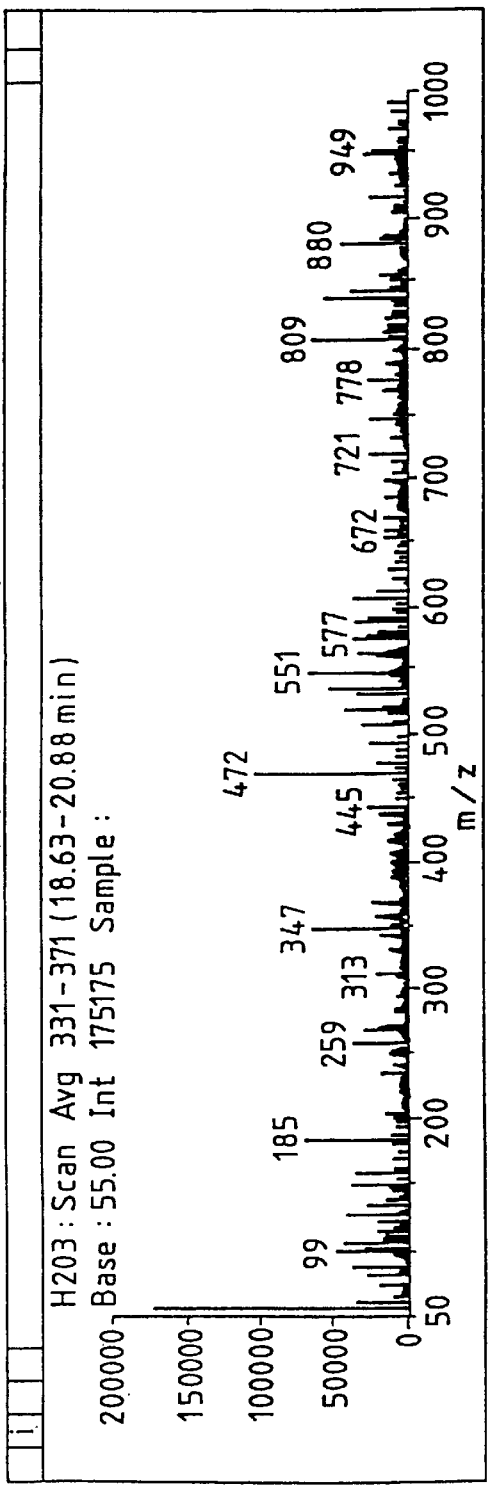
FIG. 26 is a diagram showing mass spectra.
Figure 26B:
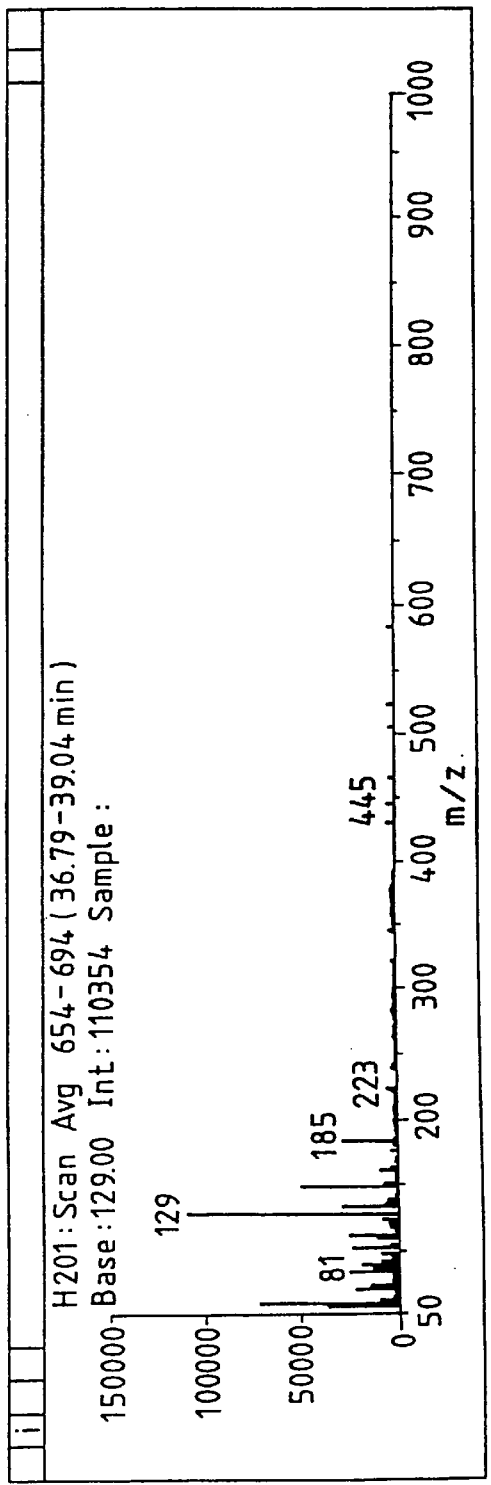

FIGS. 25 and 26 show the results of the experiment. FIG. 25 shows the results of having observed the degree of development of cluster ions under varying temperatures of the nebulizer 6 and flow rates of water, in which the axis of abscissa represents the nebulizer temperature and the axis of ordinate represents TIC. In the same figure, the marks × and ○ represent TIC values at mobile phase flow rates of 1 ml/min and 0.5 ml/min, respectively, in the absence of the turbulent flow generating plate 40, while the mark □ represent TIC values at a mobile phase flow rate of 1 ml/min in the presence of the turbulent flow generating plate 40. In the absence of the turbulent flow generating plate 40, both × and ○ are lacking in the results of measurement at 200° C. This is because when the temperature of the nebulizer 6 was dropped to below 250° C. there occurred a sudden increase of cluster ions of water and TIC became extremely unstable to an unmeasurable extent. At a nebulizer temperature of 250° C., TIC is $2\times10^7$ at a flow rate of 1 ml/min. When the flow rate is reduced to half, i.e. 0.5 ml/min, TIC also becomes half, i.e. $1\times10^7$. If the nebulizer temperature is set high, TIC (chemical noise) decreases, provided TIC does not decrease below $8\times10^6$ even at a flow rate of 0.5 ml/min and a nebulizer temperature of 350° C. Heating at a higher temperature is not applicable because there would occur thermal decomposition of the sample.

In the presence of the turbulent flow generating plate 40, TIC (chemical noise) becomes $1\times10^6$ or less, and thus in comparison with the case where the turbulent flow generating plate 40 is not used, TIC greatly decreases more than one digit at a nebulizer 6 temperature of not lower than 300° C. and two digits at a nebulizer temperature of not higher than 250° C. Besides, from 200° C. to 350° C. there is no great change in TIC. At 200° C. in the absence of the turbulent flow generating plate 40, measurement was infeasible due to too much noise. Upon mounting of the turbulent flow generating plate 40, it becomes possible to make measurement. That the measurement thus becomes possible even at a temperature below 250° C. is extremely effective because the thermal decomposition of the sample can be avoided. This is the result of micronization and uniforming of the mists attained by the turbulent flow generating plate 40.

FIG. 26 shows mass spectra obtained in the presence and absence of the turbulent flow generating plate 40, in which the mass spectra shown in the upper and lower stages have been obtained in the absence and presence, respectively, of the turbulent flow generating plate 40. Conditions for obtaining both mass spectra are the same. The flow rate of the mobile phase is 1 ml/min, the temperature of the nebulizer 6 is 250° C. and that of the vaporizer is 400° C. As shown in the same figure in the absence of the turbulent flow generating plate 40, ions of unknown source are developed in the intensity range of 100,000 to 50,000 over the m/z range of 100 to 1,000. On the other hand, in the presence of the turbulent flow generating plate 40, there appears no peak of 10,000 or more in intensity from m/z 200. It turns out that many cluster ions have been extinguished in the presence of the turbulent flow generating plate 40.

Reduced noise and being independent of the nebulizer temperature bring about the following advantage. It is not necessary to change the nebulizer temperature even for mobile phases of different compositions. This is extremely effective in gradient measurement. The nebulizer temperature can be set continuously at approximately 250° C. and thus the operability can be enhanced to a remarkable extent. Besides, as long as the nebulizer temperature is held at about 250° C., the measurement can be conducted stably while preventing the thermal decomposition of a thermally unstable substance.

Thus, it becomes possible to improve the accuracy of mass spectrometric analysis.

What is claimed is:

1. A liquid chromatograph mass spectrometer comprising:
   a liquid chromatograph;
   a nebulizer nebulizing effluent from said liquid chromatograph;
   a heater including a passage heating mists resulting from said nebulizer by heat conduction wherein said passage has a bent formation such that a flow direction of the bent passage differs from a flow direction of the nebulized mist thereby stirring the mist;
   an ionizer ionizing the heated mists; and
   a mass spectrometer for mass spectrometric analysis of the resulting ions.

2. A liquid chromatograph mass spectrometer comprising:
   a liquid chromatograph;
   a nebulizer nebulizing effluent from said liquid chromatograph;
   a heater heating mists resulting from said nebulizer;
   an ionizer ionizing the heated mists;
   a mass spectrometer providing mass spectrometric analysis of the resulting ions; and
   a stirrer stirring almost all of the mists during said heating of the mists.

3. A liquid chromatograph mass spectrometer comprising:
   a liquid chromatograph;
   a nebulizer nebulizing effluent from said liquid chromatograph;
   a heater heating mists resulting from said nebulizer by heat conduction wherein said heater includes an obstructing object used to create a turbulent flow in a downstream direction of the heated mist thereby stirring the mist;
   an ionizer ionizing the heated mists; and
   a mass spectrometer for mass spectrometric analysis of the resulting ions.

4. A liquid chromatograph mass spectrometer comprising:
   a liquid chromatograph;
   a nebulizer nebulizing effluent from said liquid chromatograph;
   a heater including an obstructing object used to create a turbulent flow in a downstream direction of the heated effluent;
   an ionizer ionizing mists resulting from said nebulizer;
   a mass spectrometer providing mass spectrometric analysis of the resulting ions; and
   a selector selecting a portion of the mists.

\* \* \* \* \*